United States Patent
Marks et al.

(10) Patent No.: US 12,056,870 B2
(45) Date of Patent: Aug. 6, 2024

(54) SYSTEM AND METHOD FOR REMOTE MEASUREMENTS OF VITAL SIGNS OF A PERSON IN A VOLATILE ENVIRONMENT

(71) Applicants: Mitsubishi Electric Research Laboratories, Inc., Cambridge, MA (US); Mitsubishi Electric Corporation, Tokyo (JP)

(72) Inventors: Tim Marks, Newton, MA (US); Hassan Mansour, Boston, MA (US); Ewa Nowara, Boston, MA (US); Yudai Nakamura, Tokyo (JP); Ashok Veeraghavan, Boston, MA (US)

(73) Assignees: Mitsubishi Electric Research Laboratories, Inc.; Mitsubishi Electric Corporation, Tokyo (JP)

( * ) Notice: Subject to any disclaimer, the term of this patent is extended or adjusted under 35 U.S.C. 154(b) by 818 days.

(21) Appl. No.: 17/199,696

(22) Filed: Mar. 12, 2021

(65) Prior Publication Data
US 2021/0224983 A1   Jul. 22, 2021

Related U.S. Application Data

(63) Continuation-in-part of application No. 16/167,668, filed on Oct. 23, 2018, now Pat. No. 11,259,710.

(Continued)

(51) Int. Cl.
*G06T 5/20* (2006.01)
*A61B 5/00* (2006.01)
(Continued)

(52) U.S. Cl.
CPC .............. *G06T 7/0012* (2013.01); *G06T 5/20* (2013.01); *G06T 5/70* (2024.01); *A61B 5/0022* (2013.01);
(Continued)

(58) Field of Classification Search
CPC . A61B 5/0059; A61B 5/02416; A61B 5/1455; A61B 5/7235; A61B 5/7271;
(Continued)

(56) References Cited

U.S. PATENT DOCUMENTS

2014/0293053 A1* 10/2014 Chuang ................ A61B 5/6893
348/148
2014/0303454 A1* 10/2014 Clifton ................. A61B 5/0205
600/479

(Continued)

OTHER PUBLICATIONS

Xinchi et al. Noncontact Monitoring of heart rate and heart rate variability in geriatric patients using photoplethysmography imagins. XP011854101.

*Primary Examiner* — Eric F Winakur
(74) *Attorney, Agent, or Firm* — Gene Vinokur; Hironori Tsukamoto

(57) ABSTRACT

A remote photoplethysmography (RPPG) system for estimating vital signs of a person is provided. The RPPG system is configured to receive a set of imaging photoplethysmography (iPPG) signals measured from different regions of a skin of a person. The RPPG system is further configured to determine frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have the non-zero values at the same frequency bins; and output one or a combination of the determined frequency coefficients, the iPPG signals reconstructed from the determined frequency coefficients, and a vital sign signal corresponding to the reconstructed iPPG signals.

24 Claims, 19 Drawing Sheets

Related U.S. Application Data

(60) Provisional application No. 62/672,433, filed on May 16, 2018.

(51) Int. Cl.
*A61B 5/024* (2006.01)
*B60Q 9/00* (2006.01)
*B60T 7/12* (2006.01)
*B60W 30/182* (2020.01)
*B62D 6/00* (2006.01)
*G06T 5/70* (2024.01)
*G06T 7/00* (2017.01)

(52) U.S. Cl.
CPC ............ *A61B 5/02416* (2013.01); *B60Q 9/00* (2013.01); *B60T 7/12* (2013.01); *B60W 30/182* (2013.01); *B60W 2540/221* (2020.02); *B62D 6/00* (2013.01); *G06T 2207/10048* (2013.01); *G06T 2207/30076* (2013.01); *G06T 2207/30088* (2013.01); *G06T 2207/30104* (2013.01); *G06T 2207/30268* (2013.01)

(58) Field of Classification Search
CPC ................. G06T 7/0012; G06T 7/0016; G06T 2007/30076; G06T 2007/30268
See application file for complete search history.

(56) References Cited

U.S. PATENT DOCUMENTS

| | | | |
|---|---|---|---|
| 2017/0367590 A1* | 12/2017 | Sebe | A61B 5/024 |
| 2018/0307927 A1* | 10/2018 | Hutchinson | A61B 5/7207 |
| 2019/0239761 A1* | 8/2019 | Tao | A61B 5/02416 |
| 2019/0350471 A1 | 11/2019 | Marks et al. | |
| 2021/0219848 A1* | 7/2021 | Hong | A61B 5/024 |
| 2021/0224983 A1 | 7/2021 | Marks et al. | |

\* cited by examiner

Algorithm 1 AutoSparsePPG algorithm

Input: $Z, X^0, E^0, \alpha$

Set: $r_0 = \|X^0\|_{2,1} + \mu\|E^{0T}\|_{2,1}$

1: $\nabla X^0 \leftarrow F(Z - E^0)$
2: $\nabla E^0 \leftarrow X^0 - Z$
3: $t_0 \leftarrow \frac{\max\|X_0\|_{2,\infty}}{\|\nabla_{E_0}\|_{2,\infty}}$
4: for $k = 1$ to $K$ do
5: $\tilde{X}^k \leftarrow X^{k-1} - \alpha \nabla X^{k-1}$
6: $\tilde{E}^k \leftarrow E^{k-1} - \alpha \nabla E^{k-1}$
7: $(X^k, E^k) \leftarrow \text{proj}_{2,1}(\tilde{X}^k, \tilde{E}^k, \tau)$
8: $\nabla X^k \leftarrow F(Z - E^k)$
9: $\nabla E^k \leftarrow X^k - Z$ return: $X^K, E^K$

FIG. 2A

Algorithm 2 $\text{proj}_{2,1}$ : constrained $\ell_{2,1}$ projector input: $X, E, \tau, \alpha$.
set: $\lambda \leftarrow 0, \tilde{X} \leftarrow X, \tilde{E} \leftarrow E$
define: $R(X, E) := \|X\|_{2,1} + \mu \|E^T\|_{2,1}$
Compute row and column norms
$X_r \leftarrow [\|X(1,:)\|_2, \ldots, \|X(T,:)\|_2]^T$
$E_c \leftarrow [\|E(:,1)\|_2, \ldots, \|E(:,J)\|_2]$
3: while $R(X, E) > \tau$ do
   Apply soft-thresholding
4: $X \leftarrow \frac{X}{X_r} \odot \max\{X_r - \alpha\lambda, 0\}$
5: $E \leftarrow \frac{E}{E_c} \odot \max\{E_c - \mu\alpha\lambda, 0\}$
   Compute row and column norms
6: $X_r \leftarrow [\|X(1,:)\|_2, \ldots, \|X(T,:)\|_2]^T$
7: $E_c \leftarrow [\|E(:,1)\|_2, \ldots, \|E(:,J)\|_2]$
   Update $\lambda$
8: $g \leftarrow -\|X_r\|_b - \mu\|E_c\|_b$
9: $\lambda \leftarrow \max\left\{0, \lambda - \frac{R(X,E)-\tau}{g}\right\}$ return: $X, E$

FIG. 2B

SYSTEM AND METHOD FOR REMOTE MEASUREMENTS OF VITAL SIGNS OF A PERSON IN A VOLATILE ENVIRONMENT

CROSS-REFERENCE TO RELATED APPLICATIONS

This application is a continuation-in-part of U.S. patent application US20190350471A1, filed on Oct. 23, 2018, which claims the priority benefit of Provisional application No. 62/672,433, filed on May 16, 2018 the contents of which are incorporated herein by reference in its entirety.

TECHNICAL FIELD

The present disclosure relates generally to remotely monitoring vital signs of a person and more particularly to remote photoplethysmography (RPPG) measurements of the vital signs of a person present in a volatile environment.

BACKGROUND

Vital signs of a person, for example the heart rate (HR), the heart rate variability (HRV), the respiration rate (RR), or the blood oxygen saturation, serve as indicators of a person's current state and as a potential predictor of serious medical events. For this reason, vital signs are extensively monitored in inpatient and outpatient care settings, at home, and in other health, leisure, and fitness settings. One way of measuring the vital signs is plethysmography. Plethysmography generally refers to measurement of volume changes of an organ or a body part and in particular to detection of volume changes due to a cardiovascular pulse wave traveling through the body of a person with every heartbeat.

Photoplethysmography (PPG) is an optical measurement technique that evaluates a time-variant change of light reflectance or transmission of an area or volume of interest, which can be used to detect blood volume changes in microvascular bed of tissue. PPG is based on a principle that blood absorbs and reflects light differently than surrounding tissue, so variations in the blood volume with every heartbeat affect light transmission or reflectance correspondingly. PPG is often used non-invasively to make measurements at the skin surface. The PPG waveform includes a pulsatile physiological waveform attributed to cardiac synchronous changes in the blood volume with each heartbeat, and is superimposed on a slowly varying baseline with various lower frequency components attributed to other factors such as respiration, sympathetic nervous system activity, and thermoregulation. Although the origins of the components of the PPG signal are not fully understood, it is generally accepted that they can provide valuable information about the cardiovascular system.

Conventional pulse oximeters for measuring the heart rate and the (arterial) blood oxygen saturation of a person are attached to the skin of the person, for instance to a fingertip, earlobe, or forehead. Therefore, they are referred to as 'contact' PPG devices. A typical pulse oximeter can include a combination of a green LED, a blue LED, a red LED, and an infrared LED as light sources and one photodiode for detecting light that has been transmitted through patient tissue. Commercially available pulse oximeters quickly switch between measurements at different wavelengths and thereby measure the transmissivity of the same area or volume of tissue at different wavelengths. This is referred to as time-division-multiplexing. The transmissivity over time at each wavelength yields the PPG signals for different wavelengths. Although contact PPG is regarded as a basically non-invasive technique, contact PPG measurement is often experienced as being unpleasant, since the pulse oximeter is directly attached to the person and any cables limit freedom to move.

Recently, non-contact, remote PPG (RPPG) for unobtrusive measurements has been introduced. RPPG utilizes light sources or, in general, radiation sources disposed remotely from the person of interest. Similarly, a detector, e.g., a camera or a photo detector, can be disposed remotely from the person of interest. RPPG is also often referred to as imaging PPG (iPPG), due to its use of imaging sensors such as cameras. We use the terms RPPG and iPPG interchangeably. Because they do not require direct contact with a person, remote photoplethysmographic systems and devices are considered unobtrusive and are in that sense well suited for medical as well as non-medical everyday applications.

One advantage of camera-based vital signs monitoring versus on-body sensors is ease of use. There is no need to attach a sensor to the person, as aiming the camera at the person is sufficient. Another advantage of camera-based vital signs monitoring over on-body sensors is that cameras have greater spatial resolution than contact sensors, which mostly include a single-element detector.

One of the challenges for RPPG technology is to be able to provide accurate measurements in a volatile environment where there exist unique sources of noise. For example, in a volatile environment such as in-vehicle environment, illumination on a driver varies drastically and suddenly during driving (e.g., while driving through shadows of buildings, trees, etc.), making it difficult to distinguish iPPG signals from other intensity variations. Also, there is significant motion of driver's head and face due to a number of factors, such as motion of the vehicle, the driver looking around both within and outside the car (for oncoming traffic, looking into rear-view mirrors and side-view mirrors, etc.), and the like.

Several methods have been developed to enable robust camera-based vital signs measurement. For such measurements, usually a plurality of signals is captured based on image processing of a captured image sequence. For example, plurality of signals may originate from different color channels of a video sequence. Then, photoplethysmographic signals are derived from the plurality of the signals. These photoplethysmographic signals are indicative of the vital signs of a person that can be determined by further analysis of the signals. However, quality of the photoplethysmographic signals is degraded to an extent determined by values of signal-to-noise ratio (SNR) of sensed measurements. Low SNR due to illumination variations and false peaks in the photoplethysmographic signals due to motion have the potential to confound the PPG signal.

Accordingly, there is a need for a RPPG system which is robust to noise such as the illumination variations and the motion of the person.

SUMMARY

It is an object of some embodiments to estimate vital signs of a person using remote photoplethysmography (RPPG). It is also an objective of some embodiments to design an algorithm to enable robustness to motion noise. Further, it is an object of some embodiments to design a narrow-band near-infrared (NIR) system and determine a wavelength range that reduces illumination variations. Additionally or alternatively, some embodiments aim to denoise noisy imaging photoplethysmography (iPPG) signals in a set of iPPG signals measured from different regions of a skin of a person by projecting the noisy iPPG signals onto an orthogonal complement of a noise subspace.

Some embodiments are based on recognition that sensitivity of the RPPG signals to noise in the measurements of intensities (e.g., pixel intensities in camera images) of a skin of a person is caused at least in part by independent estimation of photoplethysmographic signals from the intensities of a skin of a person measured at different spatial positions. Some embodiments are based on recognition that at different locations, e.g., at different regions of the skin of the person, the measurement intensities can be subjected to different measurement noise. When photoplethysmographic signals are independently estimated from intensities at each location (e.g., the photoplethysmographic signal estimated from intensities at one skin region is estimated independently of the intensities or estimated signals from other skin regions), the independence of the different estimates may cause an estimator to fail to identify such noise.

Some embodiments are based on recognition that the measured intensities at different regions of the skin of the person can be subjected to different and sometimes even unrelated noise. The noise includes one or more of illumination variations, motion of the person, and the like. In contrast, heartbeat is a common source of the intensity variations present in the different regions of the skin. Thus, the effect of the noise on the quality of the vital signs estimation can be reduced when the independent estimation is replaced by a joint estimation of photoplethysmographic signals measured from the intensities at different regions of the skin of the person. In this way, the embodiments can extract the photoplethysmographic signal that is common to many skin regions (including regions that may also contain considerable noise), while ignoring noise signals that are not shared across many skin regions.

Some embodiments are based on recognition that it can be beneficial to estimate the photoplethysmographic signals of the different skin regions collectively, i.e., using a common metric. Some embodiments are based on recognition that two types of noise are acting on the intensities of the skin, i.e., external noise and internal noise. The external noise affects the intensity of the skin due to external factors such as lighting variations, motion of the person, and resolution of the sensor measuring the intensities. The internal noise affects the intensity of the skin due to internal factors such as different effects of cardiovascular blood flow on appearance of different regions of the skin of the person. For example, the heartbeat can affect the intensity of the forehead and cheeks of the person more than it affects the intensity of the nose.

Some embodiments are based on realization that both types of the noise can be addressed in the frequency domain of the intensity measurements. Specifically, the external noise is often non-periodic or has a periodic frequency different than that of a signal of interest (e.g., pulsatile signal), and thus can be detected in the frequency domain. On the other hand, the internal noise, while resulting in intensity variations or time-shifts of the intensity variations in different regions of the skin, preserves the periodicity of the common source of the intensity variations in the frequency domain.

To that end, some embodiments are based on realization that the common metric used to estimate the photoplethysmographic signals of the different skin regions should be enforced in the frequency domain of the intensity measurements, rather than in the time domain in which the intensity measurements were collected. In addition, joint sparsity of frequency coefficients forces different photoplethysmographic signals to be sparse together in the same frequency bins and/or to have large energy only in the same frequency bins of a quantized frequency spectrum of the measured iPPG signals. A frequency bin is a segment of the frequency axis that collects the amplitude, magnitude or energy from a small range of frequencies. Therefore, the joint sparsity adequately reflects the notion of the common source of intensity variations used by some embodiments.

Some embodiments are based on realization that since some vital signs, such as a heartbeat signal, are locally periodic and exist within all regions, this common metric should be enforced in the frequency domain. However, the intensity measurements can be affected by noise that is also periodic. Therefore, if the frequency coefficients of the photoplethysmographic signals are directly derived from the intensity measurements at each location (e.g., in each region of the skin), such a direct estimation does not easily lend itself to the enforcement of a common metric in the frequency domain.

However, some embodiments are based on another realization that direct estimation of the photoplethysmographic signals, in which the signals are derived directly from the intensity measurements, can be replaced with an optimization problem to reconstruct the frequency coefficients of the photoplethysmographic signals to match the measured intensities, rather than to directly compute the frequency coefficients from the measured intensities. Such a reverse direction in the estimation of the frequency coefficients allows performing the reconstruction subject to constraints that can enforce the common metric, i.e., the joint sparsity, on the frequency coefficients of different photoplethysmographic signals of different regions.

To that end, some embodiments determine the frequency coefficients of photoplethysmographic signals of intensity signals of different regions of a person's skin in a way that minimizes the difference between the corresponding intensity signals estimated using the determined frequency coefficients and the measured intensity signals, while enforcing the joint sparsity on the determined frequency coefficients. For example, some embodiments estimate the intensity signals using an inverse Fourier transformation of the determined frequency coefficients. Such a reverse reconstruction allows reducing the sensitivity of the RPPG estimation to the measurement noise.

Some embodiments enforce the joint sparsity as a soft constraint of the optimization problem, such that enforcing joint sparsity forces the estimated frequency coefficients to have non-zero values in only a small number of frequency bins, such that non-zero frequency bins (i.e., frequency bins having non-zero values of the frequency coefficients) are the same frequency bins across all facial regions. To that end, the joint sparsity enforcement forces the frequency bins to have the frequency coefficients of non-zero values or of zero value. The non-zero values of the frequency coefficients may be different. However, the joint sparsity enforcement does not indicate how many frequency bins are allowed to have the frequency coefficients of non-zero values or zero value.

Some embodiments are based on realization that such information can be determined by determining a sparsity level constraint. The sparsity level constraint is indicative of the number of frequency bins having non-zero values of the frequency coefficients. Specifically, the sparsity level constraint directs that a sum of frequency bin norms (or row norms of a frequency matrix) should be bounded by the sparsity level constraint. The sparsity level constraint is determined adaptively based on a function of intensities in the measured iPPG signals as a bound on the minimum energy that the jointly sparse signal embedded in the measured iPPG signals can hold. In an embodiment, the bound on the minimum energy of the jointly sparse signal is determined iteratively by minimizing energy deviation based on a gradient of the distance of the reconstructed iPPG signals to the measured iPPG signals. The gradient is computed with respect to one of the frequency coefficients or the measurement noise. The sparsity level constraint enforces an upper bound on energy levels of the determined frequency coefficients of the reconstructed iPPG signals. The sparsity level constraint is enforced by a regularization parameter that is determined iteratively in response to updated estimates of the reconstructed iPPG signals to ensure that energy of the frequency coefficients of the reconstructed iPPG signals equals the sparsity level constraint.

To that end, some embodiments determine the frequency coefficients at the frequency bins of the quantized frequency spectrum of the measured iPPG signals by minimizing a distance between the measured iPPG signals and corresponding iPPG signals reconstructed from the determined frequency coefficients, while enforcing the joint sparsity of the determined frequency coefficients subject to the sparsity level constraint, such that the determined frequency coefficients of different iPPG signals have the non-zero values at the same frequency bins.

Some embodiments determine weights of the frequency bins that are indicative of which frequency bins have the frequency coefficients with the non-zero values. In some embodiments, the weights of the frequency bins are determined based on a function of the phase difference across the measured iPPG signals. Some embodiments enforce the joint sparsity of the determined frequency coefficients subject to the sparsity level constraint using the weights of the frequency bins. For example, in some implementations, such a joint sparsity enforcement encourages the number of non-zero frequency coefficients indicated by the sparsity level constraint to be at the locations indicated by the frequency bins with the smaller weights.

Some embodiments are based on recognition that quantization noise of a camera can be reduced by spatial averaging of groups of pixels. To that end, a set of iPPG signals measured from a video of the person are obtained by averaging pixel intensity over all pixels in each of a set of skin regions of the person at each time step (e.g., each video frame). In some embodiments, the skin regions are facial regions that are focused around forehead, cheeks, and chin area of the face of the person. The skin regions are also referred to as "mean regions" because the iPPG signal obtained from each region is computed as a mean of the intensities of pixels in the region. To obtain the locations of the facial regions, some embodiments first use a face alignment (i.e., facial landmark detection) method to detect a number of facial landmarks, then interpolate and extrapolate the detected landmarks to a number of interpolated locations that are used to subdivide the face into more regions.

For robustness to small variations in facial regions' positions over time, some embodiments group the mean regions into a number of larger regions using a spatial median to produce a clustering of iPPG signals. Such larger regions are referred to as "median regions." A measured iPPG signal for each median region is obtained by computing for each time step a median across the iPPG signals from the mean regions that make up the median region.

Different facial regions may be contaminated differently by noise caused by changes in ambient illumination, motion alignment errors, and facial expressions, and as a result the noise may be high-dimensional. To that end, the iPPG signals from such noisy regions are also noisy. However, blood flows through facial regions with approximately a same temporal profile during a cardiac cycle. As a result, the underlying iPPG signal present in the measured intensity variations from all the median regions when grouped into a matrix corresponds to a low-rank matrix.

Some embodiments are based on realization that orthogonal projection (OP) of noisy iPPG signals can be used to suppress the noise that is contaminating the iPPG signal. In other words, the noisy iPPG signals can be denoised by using orthogonal projection (OP) of the noisy iPPG signals. To that end, some embodiments orthogonally project the noisy iPPG signals onto a noise subspace and subtract that projection from the noisy iPPG signals. This is equivalent to projecting the noisy iPPG signal onto the orthogonal complement of the noise subspace. In some embodiments, the noise subspace includes one or more of a vertical motion signal capturing a vertical motion of the regions producing the iPPG signals, a horizontal motion signal capturing a horizontal motion of the regions producing the iPPG signals, and a background illumination signal capturing light variation in background regions outside of the regions producing the iPPG signals.

Some embodiments aim to provide accurate estimation of the vital signs even in volatile environments where there is dramatic illumination variation. For example, in a volatile environment such as an in-vehicle environment, some embodiments provide an RPPG system suitable for estimating vital signs of a driver or passenger of a vehicle. However, during driving, illumination on a person's face can change dramatically. To address these challenges, additionally or alternatively to sparse reconstruction with joint sparsity disclosed above, one embodiment uses active in-car illumination, in a narrow spectral band in which the sunlight, streetlamp, and headlight and taillight spectral energy are all minimal. For example, due to the water in the atmosphere, the sunlight that reaches the earth's surface has much less energy around the near-infrared (NIR) wavelength of 940 nm than it does at other wavelengths. The light output by streetlamps and vehicle lights is typically in the visible spectrum, with very little power at infrared frequencies. To that end, one embodiment uses an active narrow-band illumination source at or near 940 nm and a camera filter at the same frequency, which ensures that much of the illumination changes due to environmental ambient illumination are filtered away. Further, since this narrow frequency band is beyond the visible range, humans do not perceive this light source and thus are not distracted by its presence. Moreover, the narrower the bandwidth of the light source used in the active illumination, the narrower the bandpass filter on the camera can be, which further rejects intensity changes due to ambient illumination.

Accordingly, one embodiment uses a narrow-bandwidth near-infrared (NIR) light source to illuminate the skin of the person at a narrow frequency band including a near-infrared wavelength of 940 nm and an NIR camera with a narrow-band filter overlapping the wavelengths of the narrow-band light source to measure the intensities of different regions of the skin in the narrow frequency band.

One embodiment discloses a remote photoplethysmography (RPPG) system for estimating vital signs of a person. The RPPG system comprises at least one processor and a memory having instructions stored thereon that, when executed by the at least one processor, cause the RPPG system to: receive a set of imaging photoplethysmography (iPPG) signals measured from different regions of a skin of a person; determine a sparsity level constraint indicative of a number of frequency bins of a quantized frequency spectrum of the measured iPPG signals having non-zero values of frequency coefficients; determine frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have non-zero values at the same frequency bins; and output one or a combination of the determined frequency coefficients, the iPPG signals reconstructed from the determined frequency coefficients, and a vital sign signal corresponding to the reconstructed iPPG signals.

Another embodiment discloses a remote photoplethysmography (RPPG) method for estimating vital signs of a person. The RPPG method comprises: receiving a set of imaging photoplethysmography (iPPG) signals measured from different regions of a skin of a person; determining a sparsity level constraint indicative of a number of frequency bins of a quantized frequency spectrum of the measured iPPG signals having non-zero values of frequency coefficients; determining frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have the non-zero values at the same frequency bins; and outputting one or a combination of the determined frequency coefficients, the iPPG signals reconstructed from the determined frequency coefficients, and a vital sign signal corresponding to the reconstructed iPPG signals.

BRIEF DESCRIPTION OF THE DRAWINGS

FIG. 2A shows a schematic of an AutoSparsePPG algorithm for sparse spectrum estimation, according to some embodiments.

FIG. 2B shows a schematic of an algorithm for the two-one norm regularization step of the AutoSparsePPG algorithm, according to some embodiments.

DETAILED DESCRIPTION

In the following description, for purposes of explanation, numerous specific details are set forth in order to provide a thorough understanding of the present disclosure. It will be apparent, however, to one skilled in the art that the present disclosure may be practiced without these specific details. In other instances, apparatuses and methods are shown in block diagram form only in order to avoid obscuring the present disclosure.

As used in this specification and claims, the terms "for example," "for instance," and "such as," and the verbs "comprising," "having," "including," and their other verb forms, when used in conjunction with a listing of one or more components or other items, are each to be construed as open ended, meaning that that the listing is not to be considered as excluding other, additional components or items. The term "based on" means at least partially based on. Further, it is to be understood that the phraseology and terminology employed herein are for the purpose of the description and should not be regarded as limiting. Any heading utilized within this description is for convenience only and has no legal or limiting effect.

Figure 1A:
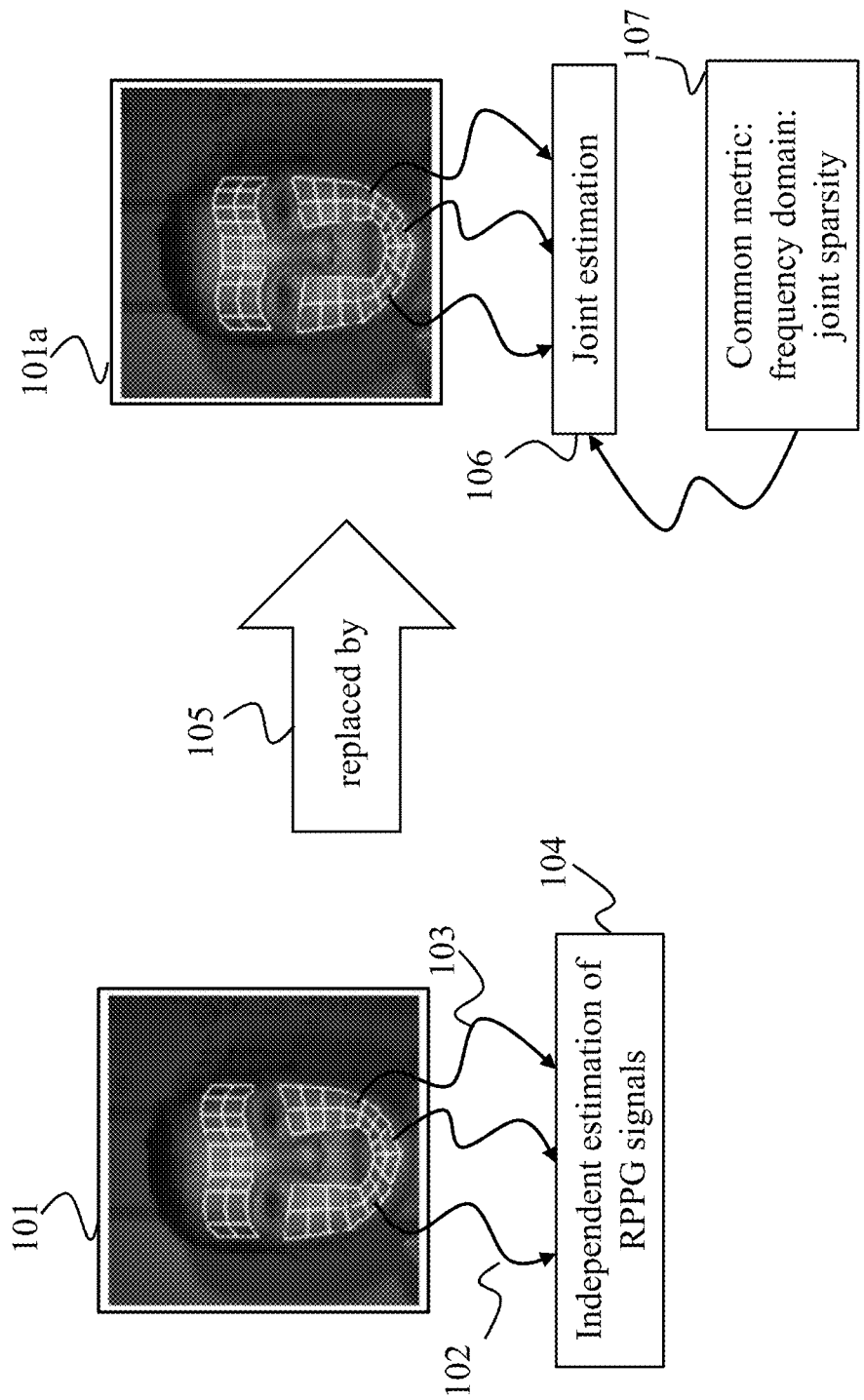
FIG. 1A shows a schematic illustrating some principles used by some embodiments to determine vital signs of the person using remote photoplethysmography (RPPG).
Figure 1B:
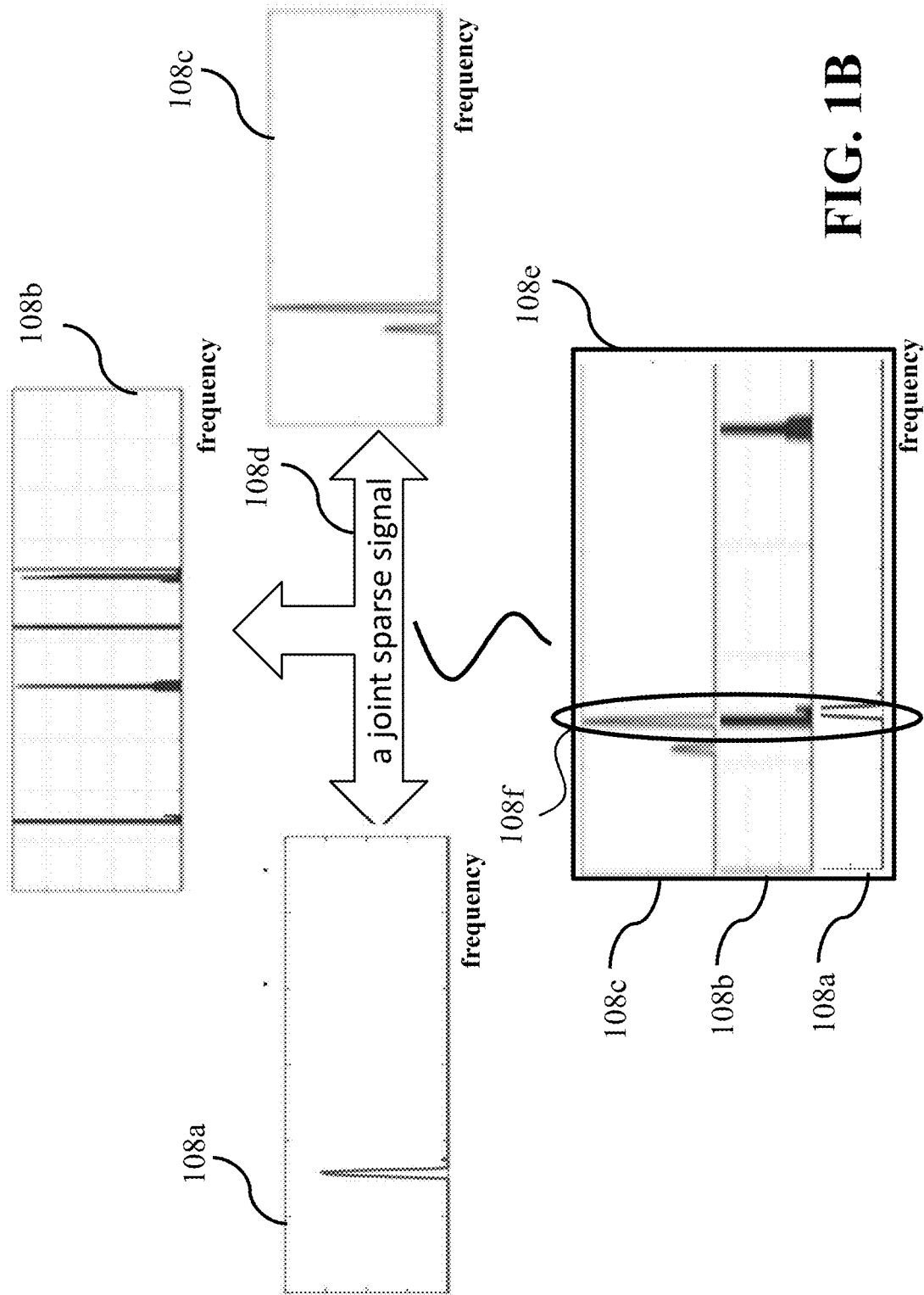
FIG. 1B shows a schematic of joint sparsity of different photoplethysmographic signals from different regions of skin of the person, according to some embodiments.

FIG. 1A shows a schematic illustrating some principles used by some embodiments to determine vital signs of a person using remote photoplethysmography (RPPG). FIG. 1B shows joint sparsity of different photoplethysmographic signals from different regions of skin of the person, according to some embodiments. FIG. 1A and FIG. 1B are explained in conjunction with each other. As blood flows through different skin regions of the person, concentration of hemoglobin changes over time. As a result, amount and color of light absorbed by the different skin regions changes. In other words, there exist intensity variations due to the blood flow. When a video of the skin regions is captured, a camera can register the intensity variations from different regions of the skin of the person. Such registered intensity variations are referred to as imaging photoplethysmography (iPPG) signals or a set of iPPG signals. Alternatively, the iPPG signals may be referred to as photoplethysmography signals or RPPG signals.

Some embodiments are based on recognition that sensitivity of RPPG signals to noise in the measurements of intensities (e.g., pixel intensities in camera images) of a skin of a person 101 is caused at least in part by independent estimation 104 of photoplethysmographic signals from the intensities 102 and 103 of a skin of a person measured at different spatial positions. Some embodiments are based on recognition that at different locations, e.g., at different regions of the skin of the person, the measurement intensities can be subjected to different measurement noise. When photoplethysmographic signals are independently estimated 104 at each location (e.g., the photoplethysmographic signal estimated from intensities at one skin region is estimated independently of the intensities or estimated signals from other skin regions), the independence of the different estimates may cause an estimator to fail to identify such noise.

FIG. 1B shows a schematic of joint sparsity of different photoplethysmographic signals from different regions of skin of the person, according to some embodiments. The frequency spectra of different photoplethysmographic signals 108a, 108b, and 108c measured from different regions of skin of the person. For ease of explanation, only three photoplethysmographic signals are considered herein.

Some embodiments are based on recognition that the photoplethysmographic signals 108a, 108b, and 108c can be subjected to different and sometimes even unrelated noise. However, heartbeat is a common source of the intensity variations present in the different regions of the skin. In other words, a jointly sparse signal 108e is embedded 108d in each of the photoplethysmographic signals 108a, 108b, and 108c. Thus, the effect of the noise on the quality of the vital signs estimation can be reduced when the independent estimation 104 of the signals from each skin region is replaced by a joint estimation 106 of photoplethysmographic signals measured from the intensities at different regions of the skin of the person. In this way, the embodiments can extract the photoplethysmographic signal that is common to many skin regions (including regions that may also contain considerable noise), while ignoring noise signals that are not shared across many skin regions.

Some embodiments are based on recognition that it can be beneficial to estimate the photoplethysmographic signals of the different skin regions collectively, i.e., a jointly sparse signal 108e (also referred as a common metric). Some embodiments are based on recognition that two types of noise are acting on the intensities of the skin, i.e., external noise and internal noise. The external noise affects the intensity of the skin due to external factors such as lighting variations, motion of the person, and resolution of the sensor measuring the intensities. The internal noise affects the intensity of the skin due to internal factors such as different effects of cardiovascular blood flow on appearance of different regions of the skin of the person. For example, the heartbeat can affect the intensity of the forehead and cheeks of the person more than it affects the intensity of the nose.

Some embodiments are based on realization that both types of the noise can be addressed in the frequency domain of the intensity measurements. Specifically, the external noise is often non-periodic or has a periodic frequency different than that of a signal of interest (e.g., pulsatile signal), and thus can be detected in the frequency domain. On the other hand, the internal noise, while resulting in intensity variations or time-shifts of the intensity variations in different regions of the skin, preserves the periodicity of the common source of the intensity variations in the frequency domain.

To that end, some embodiments are based on realization that the common metric used to estimate the photoplethysmographic signals of the different skin regions should be enforced in the frequency domain of the intensity measurements, rather than in the time domain in which the intensity measurements were collected. In addition, joint sparsity of frequency coefficients forces different photoplethysmographic signals to be sparse together in the same frequency bins, e.g., bin 108f, and/or to have large energy only in the same frequency bins of a quantized frequency spectrum of the measured iPPG signals. A frequency bin is a segment of the frequency axis that collects the amplitude, magnitude or energy from a small range of frequencies. Therefore, the joint sparsity adequately reflects the notion of the common source of intensity variations used by some embodiments.

Figure 1C:
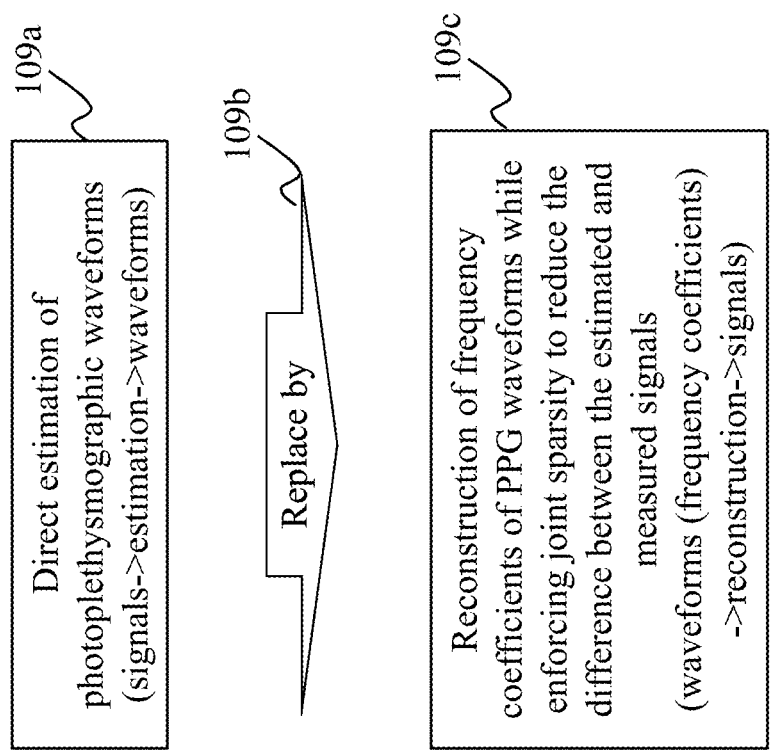
FIG. 1C shows a schematic of principles used by some embodiments to enforce the joint sparsity in frequency domain on joint estimation of photoplethysmography signals for different regions of the skin of the person.

FIG. 1C shows a schematic of principles used by some embodiments to enforce the joint sparsity in the frequency domain for the joint estimation of photoplethysmographic signals for different regions of the skin of the person. Some embodiments are based on realization that since some vital signs, such as a heartbeat signal, are locally periodic and exist within all skin regions, the common metric should be enforced in the frequency domain. However, the intensity measurements can be affected by noise that is also periodic. Therefore, if the frequency coefficients of the photoplethysmographic signals are directly derived from the intensity measurements at each location (e.g., in each region of the skin), such a direct estimation does not easily lend itself to the enforcement of a common metric in the frequency domain. However, some embodiments are based on another realization that direct estimation of the photoplethysmographic signals, in which the signals are derived directly from the intensity measurements (at 109a), can be replaced by (at 109b) an optimization framework to reconstruct the frequency coefficients of the photoplethysmographic waveforms (at 109c) to match the measured intensities, rather than to directly compute the frequency coefficients from the measured intensities. Such a reverse direction in the estimation of the frequency coefficients allows performing the reconstruction subject to constraints that can enforce the common metric, i.e., the joint sparsity, on the frequency coefficients of different photoplethysmographic signals of different regions.

Figure 1D:
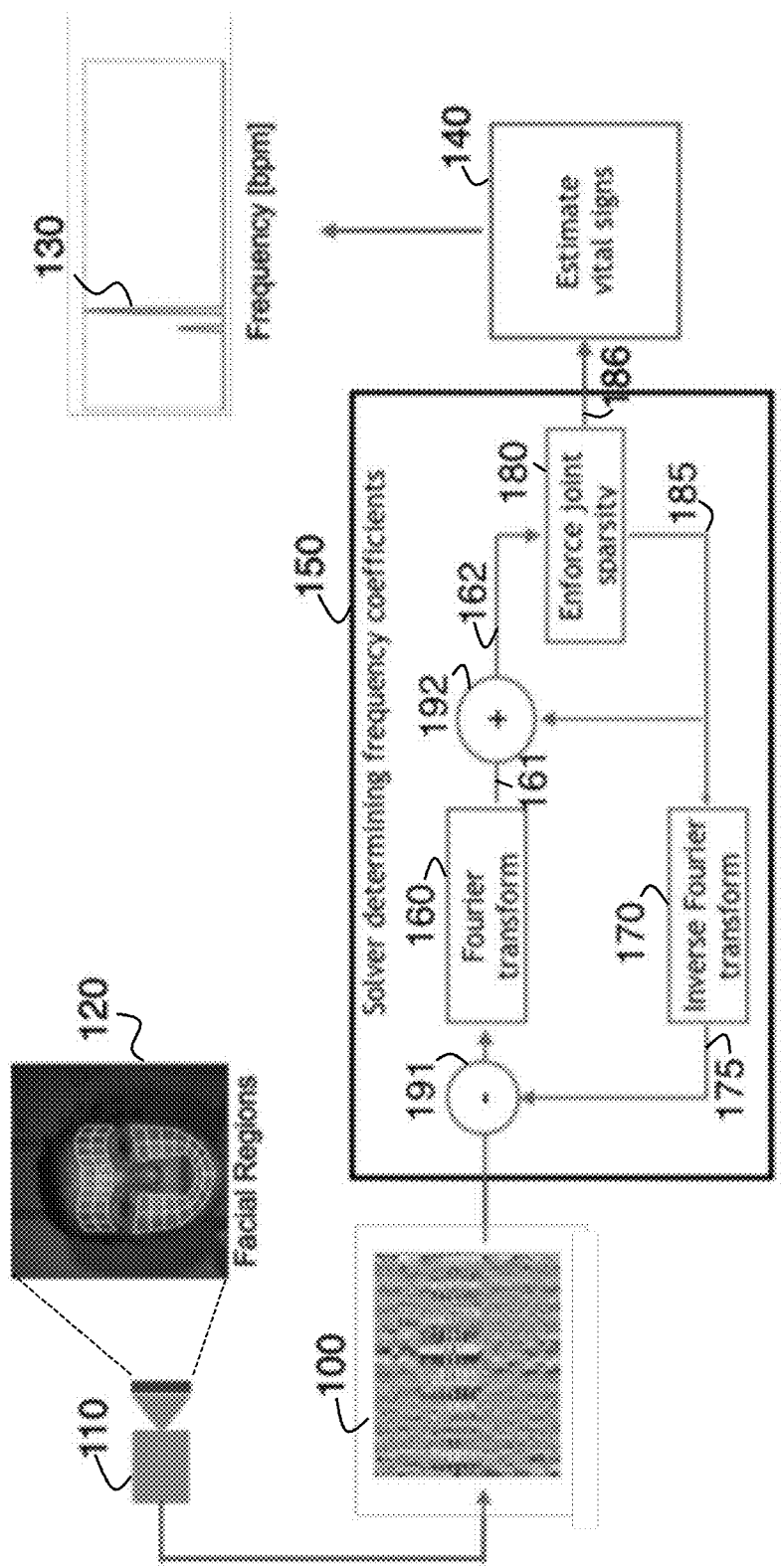
FIG. 1D shows a block diagram of an RPPG method according to one embodiment.

FIG. 1D shows a block diagram of an RPPG estimation method, according to one embodiment. A set of different skin regions 120 of a person are measured using an input interface 110, such as a video camera that measures the intensity of the light reflecting off the skin as it varies over a period of time, to produce a raw RPPG matrix 100. The diagram shows skin regions that are located on the face (facial regions), but it is understood that various embodiments are not limited to using the face; other embodiments use other regions of exposed skin, such as the person's neck or wrists. The raw RPPG matrix 100, which includes measured intensities of the facial regions over time, is processed using a solver 150 that determines frequency coefficients that correspond to the person's vital signs through an iterative process.

In some implementations, the iterative process begins by setting estimated frequency coefficients 185 of all facial regions to 0 and computing an inverse Fourier transform 170 of the frequency coefficients 185 to produce estimated region intensities 175. These estimated region intensities 175, which represent the system's estimate of the RPPG signal, are then subtracted from the raw RPPG matrix 100 to output a difference 191. The difference 191 between the raw RPPG matrix 100 and the estimated region intensities 175 is transformed using a Fourier transform 160 to produce temporary frequency coefficients 161. The temporary frequency coefficients 161 are added 192 to the estimated frequency coefficients 185 to produce updated frequency coefficients 162. The updated frequency coefficients 162 are modified to enforce joint sparsity 180, and the resulting frequency coefficients are used as the new estimated frequency coefficients 185. The new estimated frequency coefficients 185, which replace the previous iteration's estimated frequency coefficients 185, are used for a next iteration of the solver process 150.

In some embodiments, the solver 150 enforces the joint sparsity as a soft constraint of an optimization problem, such that enforcing joint sparsity 180 forces the estimated frequency coefficients 185 to have non-zero values in only a small number of frequency bins, such that non-zero frequency bins (i.e., frequency bins having non-zero values of the frequency coefficients) are the same frequency bins across all facial regions. The iterative solver process is repeated until a convergence condition 186 is met, for example, when the new estimated frequency coefficients 185 are essentially unchanged from the previous iteration's estimated frequency coefficients 185. After convergence 186, the estimated frequency coefficients 185 are output by the solver 150 and are used to estimate the vital signs 140. For example, in one embodiment an estimated vital sign 140 is the frequency of the heartbeat 130 of the person over the period of time. To that end, enforcing the joint sparsity forces the frequency coefficients to have non-zero values in only a small number of frequency bins, such that the non-zero frequency bins are the same frequency bins across all facial regions.

The joint sparsity enforcement forces the frequency bins to have the frequency coefficients of non-zero values or of zero value. The non-zero values of the frequency coefficients may be different. However, the joint sparsity enforcement does not indicate how many frequency bins are allowed to have the frequency coefficients of non-zero values or zero value.

Some embodiments are based on realization that such information can be determined by determining a sparsity level constraint. The sparsity level constraint is indicative of the number of frequency bins having non-zero values of the frequency coefficients. Specifically, the sparsity level constraint directs that a sum of frequency bin norms (or row norms of a frequency matrix) should be bounded by the sparsity level constraint. Additionally or alternatively, the sparsity level constraint is indicative of a number of frequency bins having zero values of the frequency coefficients.

Figure 1E:
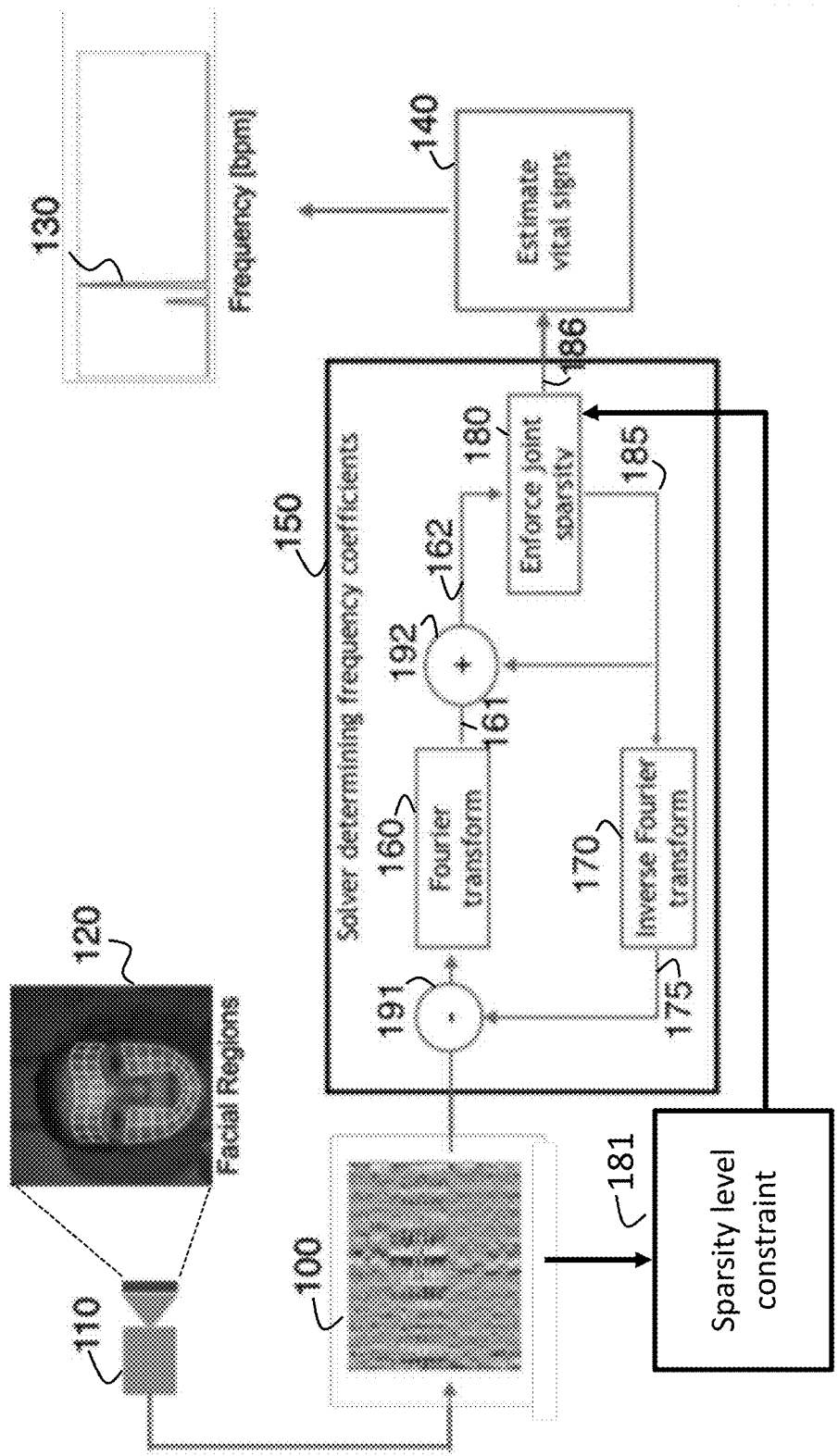
FIG. 1E shows a block diagram of an RPPG method that utilizes a sparsity level constraint, according to one embodiment.

FIG. 1E shows a block diagram of a RPPG method that utilizes the sparsity level constraint 181, according to one embodiment. The sparsity level constraint 181 is determined adaptively based on a function of intensities in the measured iPPG signals as a bound on the minimum energy that the jointly sparse signal embedded in the measured iPPG signals can hold. The determination of the sparsity level constraint is described in detail below with reference to FIGS. 2A and 2B. The sparsity level constraint 181 enforces an upper bound on energy levels of the determined frequency coefficients of the reconstructed iPPG signals. Therefore, the determined frequency coefficients 185 are subjected to the sparsity level constraint 181.

To that end, the solver 150 determines frequency coefficients at the frequency bins of the quantized frequency spectrum of the measured iPPG signals by minimizing a distance between the measured iPPG signals and corresponding iPPG signals reconstructed from the determined frequency coefficients, while enforcing the joint sparsity 180 of the determined frequency coefficients subject to the sparsity level constraint 181, such that the determined frequency coefficients of different iPPG signals have non-zero values at the same frequency bins.

The restriction of the energy levels of the determined frequency coefficients of the jointly sparse signal according to the sparsity level constraint ensures that only the jointly sparse signal attributed to the heartbeat (e.g., pulsatile) signal is estimated by the determined frequency coefficients. If the energy levels of the determined frequency coefficients were to exceed the amount prescribed by the sparsity level constraint, then periodic noise variations that exist in the measured iPPG signals would also be included in the determined frequency coefficients and thus contaminate the estimated heart rate signal. Therefore, it is imperative to limit the amount of energy of the determined frequency coefficients to the level prescribed by the sparsity level constraint. Similarly, the sparsity level constraint determines a sufficiently large energy level that the determined frequency coefficients of the jointly sparse signals should satisfy in order to estimate the heart rate signal. If the energy level of the determined frequency coefficients is too small, then the determined frequency coefficients would fail to include the entire signal corresponding to the heartbeat.

FIG. 2A shows an AutoSparsePPG algorithm for sparse spectrum estimation, according to some embodiments. The iPPG signals are quasiperiodic, which means that the iPPG signals have slowly varying frequency. Over a short time window, the heartbeat signal is approximately periodic, composed of a dominant frequency along with its harmonics. As a result, a frequency spectrum of the heartbeat signal should be sparse. Thus, some embodiments model the iPPG signals as sparse in the frequency domain. Moreover, the same heartbeat signal drives the periodic behavior in the iPPG signals across the skin regions. Therefore, the skin regions containing iPPG signal should have same sparse frequency spectrum and same support of the frequency coefficients, corresponding to an underlying noise-free vital sign (heartbeat signal). According to some embodiments, an iPPG signal Z (which in some embodiments has already been denoised using orthogonal projection, as explained in detail in the description of FIGS. 6A and 6B) is modelled as a sum of two components, namely, a desired iPPG signal Y, whose frequency matrix (or frequency spectrum) X has only a few frequency coefficients with non-zero values; and a noise matrix E. Thus, $$Z = Y + E = F^{-1}X + E,$$

where, $F^{-1}$ is the inverse Fourier transform.

A first dimension of the frequency matrix X corresponds to the different regions of the skin of the person, and a second dimension of the frequency matrix X corresponds to the frequency bins of the frequency coefficients. A first dimension of the noise matrix E corresponds to the different regions of the skin of the person, and a second dimension of the noise matrix E corresponds to the time at which the measurements were collected. In some implementations, the first dimension and second dimension of the frequency matrix X refers to columns and rows of the frequency matrix X, respectively, and the first dimension and second dimension of the noise matrix E refers to columns and rows of the noise matrix E, respectively. In some other implementations, the first dimension and second dimension of the frequency matrix X refers to rows and columns of the frequency matrix X, respectively, and the first dimension and second dimension of the noise matrix E refers to rows and columns of the noise matrix E, respectively.

Since the frequency components in the frequency matrix X should be sparse and have the same support across the skin regions, the columns (skin regions) of the frequency matrix X are jointly sparse, i.e., the entire rows (frequency bins) of the frequency matrix X are either completely zero or nonzero. Additionally, it is beneficial to ensure that the energy in the remaining skin regions is not large because the iPPG signals are weak signals and large amplitudes likely correspond to the noise. Therefore, some embodiments define the following optimization problem to compute the frequency matrix X and the noise matrix E from the denoised iPPG signal Z.

$$\min_{X,E} \frac{1}{2}\|Z - F^{-1}X - E\|_F^2 + \lambda\left(\|X\|_{2,1} + \mu\|E^T\|_{2,1}\right) \quad (1)$$

where |·| denotes Frobenius norm of a matrix. The optimization problem (1) is an $\ell_{2,1}$ norm regularization (i.e., two-one norm regularization). The $\ell_{2,1}$ norm regularization of the frequency matrix X is defined as $$\|X\|_{2,1} = \sum_i \sqrt{\sum_j X(i,j)^2},$$

The $\ell_{2,1}$ norm regularization is applied is applied to opposite dimensions of the frequency matrix X and the noise matrix E. For example, a two-norm along the columns (skin regions) of the frequency matrix X is followed by a one-norm along the rows (frequency bins) of the frequency matrix X to ensure sparsity within the computed column norms. Conversely, the two-norm of the rows (time dimension) of the noise matrix E is followed by one-norm along the columns (skin regions) of the noise matrix E to sum up the row norms and ensure sparsity across the skin regions.

In such a manner, the two-one norm regularization is applied to opposite dimensions such that two-norm along the first dimension of the frequency matrix is followed by a one-norm along the second dimension of the frequency matrix, while a two-norm along the second dimension of the noise matrix is followed by a one-norm along the first dimension of the noise matrix.

Some embodiments are based on realization that the sparsity level constraint can be enforced by a regularization parameter. The choice of regularization parameters, $\lambda$ and $\mu$, has a significant impact on the performance of heart rate (HR) estimation. According to an embodiment, changing either of aforementioned regularization parameters can lead to as much as a 30% difference in HR estimation accuracy. Moreover, very different parameter values are optimal for different videos.

Some embodiments are based on realization that the regularization parameters $\lambda$ can be selected adaptively using the AutoSparsePPG algorithm shown in FIG. 2A. For solving sparse optimization problems with least squares constraints, according to some embodiments, (1) can be rewritten as:

$$\min_{X,E} \|X - F^{-1}X - E\|_F^2$$

$$\text{subject to } \|X\|_{2,1} + \mu\|E^T\|_{2,1} < \tau,$$

where $\tau$ is defined as:

$$\tau = \tau_0 + \frac{\|Z - F^{-1}X - E\|_F^2}{\max\left(\left[\|\nabla_X\|_{2,\infty}, \mu\|\nabla_E\|_{2,\infty}\right]\right)}$$

Here, $\tau$ is the sparsity level constraint, and $\tau_0 = \|X\|_{2,1} + \mu\|E^T\|_{2,1}$ for some initial X and E. Further, $\nabla_X$ and $\nabla_E$ are the gradients of $\|Z-F^{-1}X-E\|_F^2$ with respect to X and E, respectively.

Optimization problem (2) can be solved by the AutoSparsePPG algorithm shown in FIG. 2A. Therefore, the bound on the minimum energy of the jointly sparse signal is determined iteratively by minimizing energy deviation based on a gradient of the distance of the reconstructed iPPG signals to the measured iPPG signals.

FIG. 2B shows an algorithm for the two-one norm regularization step of the AutoSparsePPG algorithm (i.e., step 7 of the AutoSparsePPG algorithm), according to some embodiments. The parameter $\lambda$ is initialized to $\lambda_0$ given by:

$$\lambda_0 = \frac{\|Z\|_F}{\sqrt{\text{card}(X)\text{card}(E)}}$$

where card is the cardinality (the number of the elements of the matrix). Further, in each iteration, $\lambda$ is updated using Newton's root finding method applied to the equation $$\|X\|_{2,1} + \mu\|E^T\|_{2,1} = \tau.$$

Consequently, the following update rule is used to modify $\lambda$ in order to satisfy $\tau$, i.e., the sparsity level constraint:

$$\lambda_{k+1} = \max\left(0, \lambda_k + \frac{\|X_{k+1}\|_{2,1} + \mu\|E_{k+1}^T\|_{2,1} - \tau}{\beta\left(\|X_{k+1}\|_{2,0} + \mu\|E_{k+1}^T\|_{2,0}\right)}\right)$$

where $\beta$ is a step size parameter, $\|X_{k+1}\|_{2,0}$ computes the number of nonzero column-norms of $X_{k+1}$, and X and E are initialized with zeros. In such a manner, the sparsity level constraint is enforced by a regularization parameter ($\lambda$) that is determined iteratively in response to updated estimates of the reconstructed iPPG signals to ensure that energy of the frequency coefficients of the reconstructed iPPG signals equals the sparsity level constraint.

To combine the denoised iPPG signals from each skin region, some embodiments compute a median in each frequency bin across the skin regions of X. A median is more robust to outliers than a mean when some of the skin regions are corrupted by the noise. A frequency component at which power in the frequency spectrum is maximum is the heart rate output by the AutoSparsePPG algorithm for a given time window.

Figure 3A:
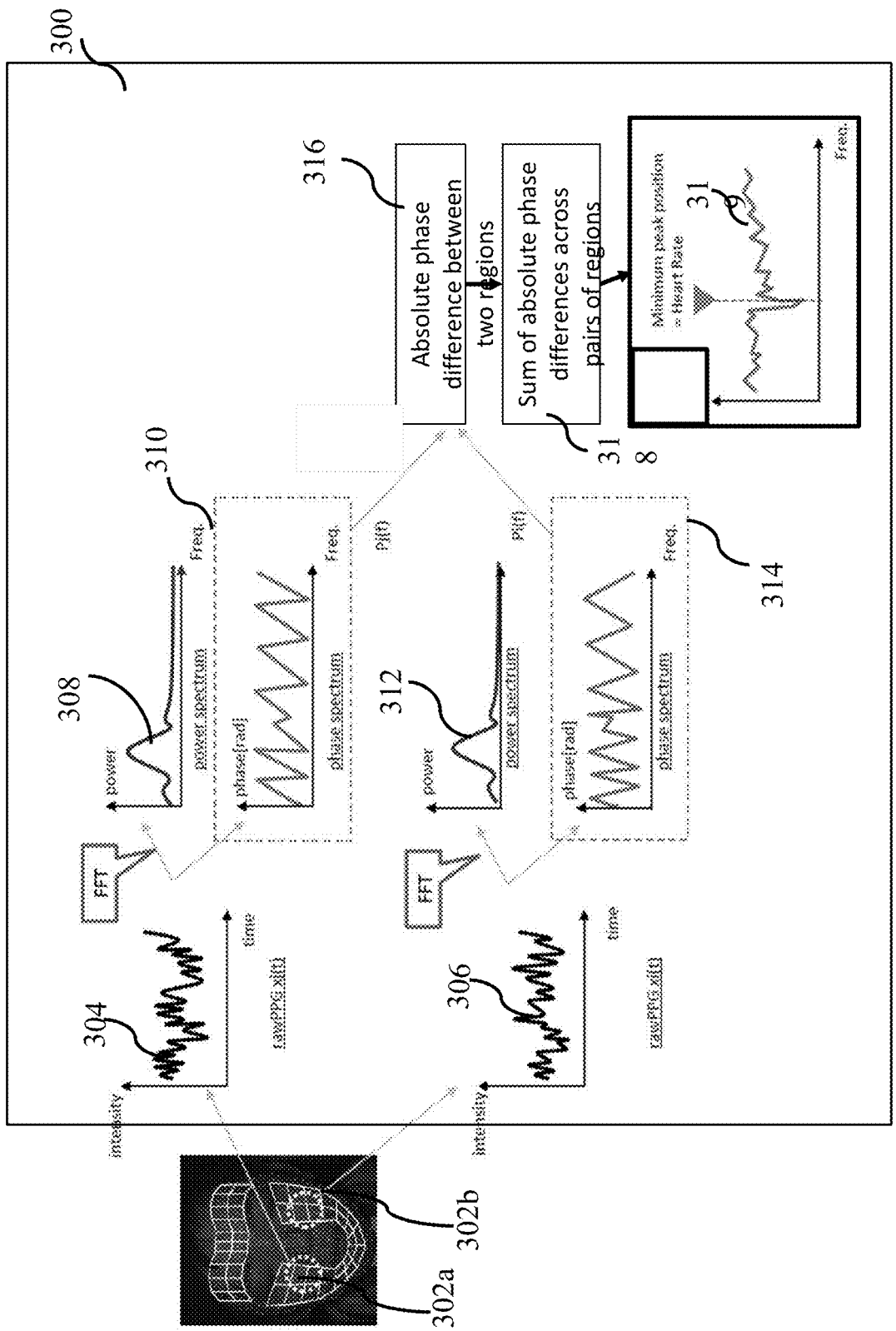
FIG. 3A shows a schematic for determining weights of frequency bins, according to some embodiments.

FIG. 3A shows a schematic for determining weights of the frequency bins, according to some embodiments. The weights of the frequency bins are indicative of which frequency bins have the frequency coefficients with the non-zero values. To determine the weights of the frequency bins, at first, a pair of skin regions 302a and 302b is considered. A weight estimator 300 is configured to obtain an iPPG signal 304 corresponding to the skin region 302a, and an iPPG signal 306 corresponding to the skin region 302b. Further, a fast Fourier transform (FFT) is applied to the iPPG signal 304. As a result, a power spectrum 308 and a phase spectrum 310 of the iPPG signal 304 are produced. Likewise, FFT is applied to the iPPG signal 306, and consequently a power spectrum 312 and a phase spectrum 314 of the iPPG signal 306 are produced.

The phase spectrum 310 of the iPPG signal 304 and the phase spectrum 314 of the iPPG signal 306 are compared. Specifically, the weight estimator 300 is configured to compute the difference between the phase spectrum 310 and the phase spectrum 314. Then the absolute value of this difference is computed in each frequency bin, to obtain the absolute phase difference 316 between the two skin regions 302a and 302b. In a similar manner, absolute phase differences across other pairs of skin regions are determined; in some embodiments, the absolute phase difference is computed for every possible pair of regions, such that for N regions, there are N(N+1)/2 pairs of regions. Further, the weight estimator 300 computes a sum 318 of the absolute phase differences across the different pairs of regions to produce a signal 319. Some embodiments are based on recognition that the heartbeat signal has approximately the same phase in different skin regions (e.g., different regions of the face), whereas many noise signals (such as those due to changes in lighting as a result of motion) have different phase in different skin regions. Accordingly, the frequency bin that has the smallest sum of absolute phase differences is likely to include the frequency of the heartbeat signal. To that end, some embodiments are based on recognition that a frequency corresponding to the heart rate has the smallest sum of absolute phase differences. The signal 319 is normalized to determine the weights for the frequency bins, such that the weights may have any value between zero and one In such a manner, the weights of the frequency bins are determined based on a function of the phase differences across the measured iPPG signals. In these embodiments, the weight of each frequency bin may be different. In other embodiments, the weights of the frequency bins may be set to identical nonzero values (e.g., all weights are set equal to 1), which is equivalent to an unweighted optimization.

Figure 3B:
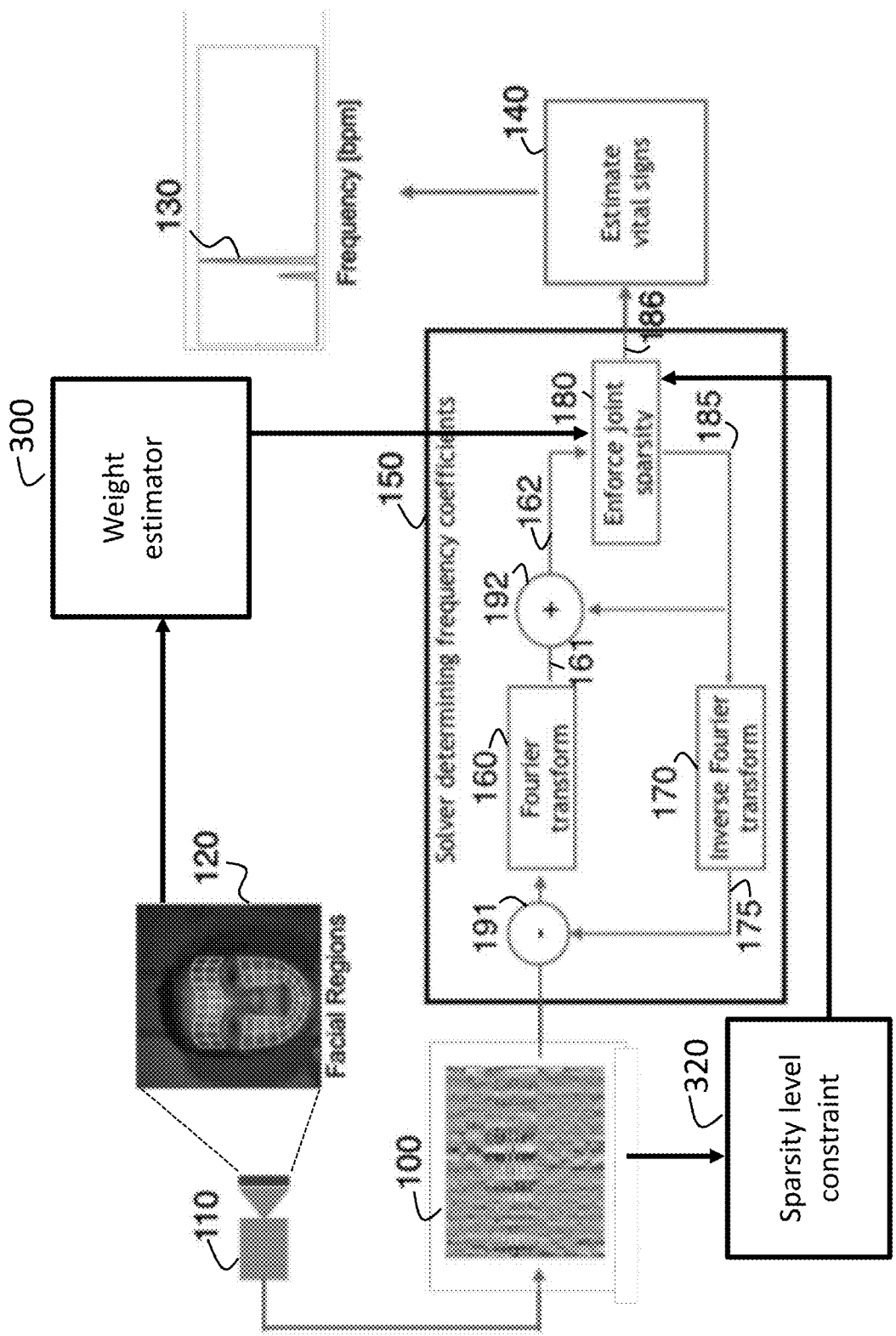
FIG. 3B shows a schematic of an RPPG method that utilizes a sparsity level constraint and a weight estimator, according to some embodiments.

FIG. 3B shows a schematic of an RPPG method that utilizes a sparsity level constraint 320 and the weight estimator 300, according to an embodiment. Some embodiments incorporate the weights in the AutoSparsePPG algorithm. As a result, instead of thresholding λ multiplied by 1, some embodiments threshold with λ multiplied by the weight for each frequency bin. To that end, the optimization problem corresponds to a weighted two-one norm regularization. The weighted two-one norm regularization is applied to opposite dimensions of the frequency matrix X and the noise matrix E.

The weighted two-one norm regularization is applied to opposite dimensions such that two-norm along the first dimension of the frequency matrix X is followed by a weighted one-norm along the second dimension of the frequency matrix X, while a two-norm along the second dimension of the noise matrix E is followed by a weighted one-norm along the first dimension of the noise matrix E. In an embodiment, weights in the weighted one-norm along the first dimension of the noise matrix are identical, and weights in the weighted one-norm along the first dimension of the noise matrix are identical. The weights in the weighted one-norm along the second dimension of the frequency matrix are a function of the phase differences across the measured iPPG signals from different regions The weight estimator 300 outputs the weights of frequency bins. The solver enforces the joint sparsity 180 of the determined frequency coefficients subject to the sparsity level constraint 320 with the weights of the frequency bins. Such a joint sparsity enforcement encourages the number of non-zero frequency coefficient indicated by the sparsity level constraint to be at the locations indicated by the frequency bins with the smallest weights.

Figure 4:
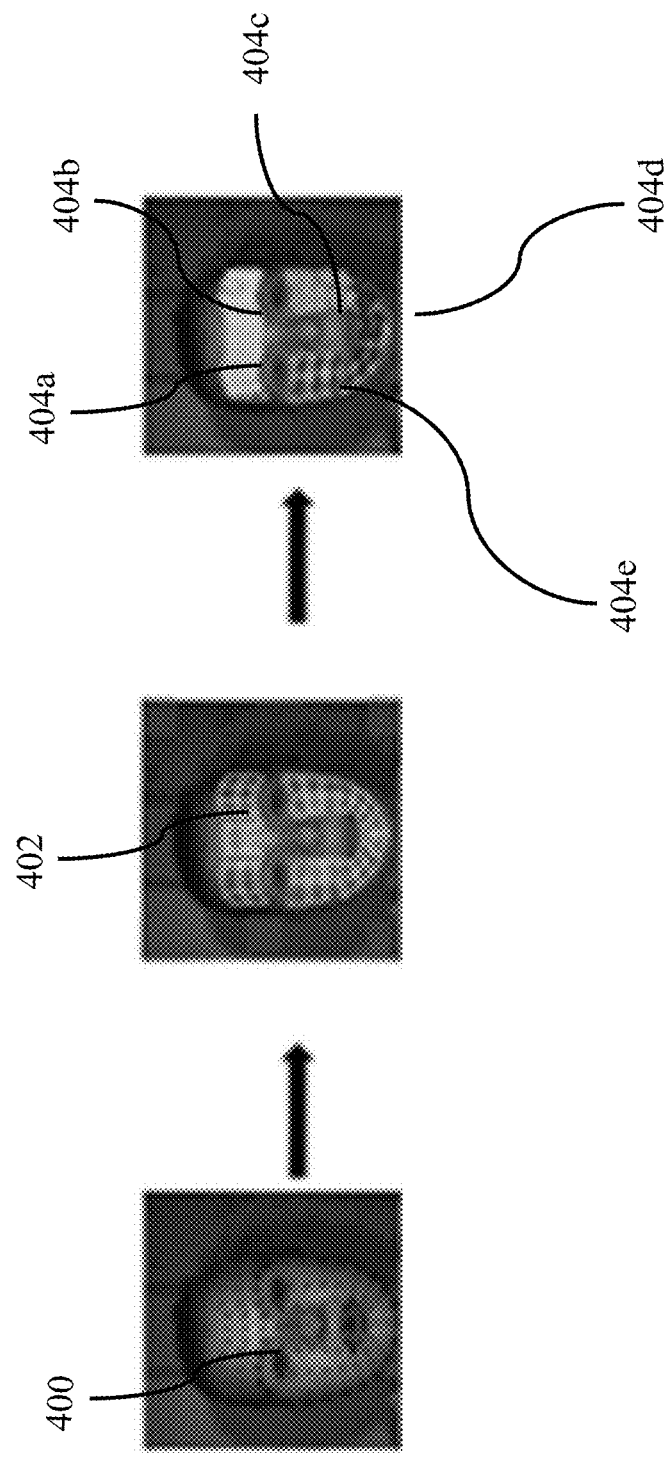
FIG. 4 illustrates computing of imaging photoplethysmography (iPPG) signals from video intensities, according to some embodiments.

FIG. 4 illustrates computing of the iPPG signals from video intensities, according to some embodiments. Some embodiments are based on recognition that quantization noise of the camera, $V_n(t)$, can be reduced by spatial averaging of groups of pixels. To that end, the RPPG method obtains a set of iPPG signals measured from a video of the person by averaging pixel intensity over all pixels in each of a set of skin regions 402 (also called N skin regions) of the person at each time step (e.g., each video frame). In some embodiments, the skin regions 402 are facial regions that are focused around forehead, cheeks, and chin area of the face of the person. In some embodiments, the RPPG method excludes regions along the face boundary as well as eyes, nose, and mouth, since these areas exhibit weak RPPG signals. The N skin regions are also referred to as "mean regions" because the iPPG signal obtained from each region is computed as a mean of the intensities of pixels in the region.

In an embodiment, the set of iPPG signals from the video frames are obtained by spatially averaging the pixel intensities within each of N=48 facial regions of interest as shown by the set of skin regions 402. To obtain N=48 facial regions, some embodiments first use a face alignment (i.e., facial landmark detection) method to detect a number (e.g., 68) of facial landmarks 400, then interpolate and extrapolate the detected landmarks to a larger number (e.g., 145) of interpolated locations that are used to subdivide the face into more regions.

For each facial region $j \in \{1, \ldots, N\}$, the iPPG signal $p_j(t)$ obtained from the average pixel intensities is a one-dimensional time series signal, where $t \in \{1, \ldots, T\}$ is a video frame index within a time window of length T frames. The iPPG signals from the N facial regions are stacked into an iPPG matrix P of size T×N. Further, the iPPG signals are processed within overlapping time windows. Some embodiments are based on understanding that it is beneficial to use time windows of length ten seconds to process the iPPG signals, as such time windows are short enough to accommodate heart rate variations, but long enough to be robust to variations in noise over time. Further, each time window's signals are normalized by subtracting the average intensity over time of each region's signals and then dividing by the corresponding average intensity. Additionally, a bandpass filter is used to restrict the signals to a cardiac frequency range that includes a physiological range of cardiac signals of interest, e.g., 42 to 240 beats per minute (bpm).

Some embodiments are based on recognition that when the facial landmarks are detected in each video frame independently, there is a high-frequency jitter in positions of the detected landmarks, even when the face is stationary. This causes the pixels included in different small facial regions to correspond to different regions on the face for each video frame, due to which the average intensities over time change and leads to small errors that affect the vital sign estimation. Some embodiments are based on realization that such a problem can be mitigated by temporal averaging of the facial landmark positions. In some embodiments, the position of each facial landmark in frame t is estimated by averaging the detected positions of the landmark from frame t−5 to t+5.

For additional robustness to small variations in facial regions' positions over time, some embodiments group the mean regions (e.g., N=48) into a number of larger regions, using a spatial median to produce a clustering of iPPG signals. Such larger regions are referred to as "median regions." A measured iPPG signal for each median region is obtained by computing for each time step a median across the iPPG signals from the mean regions that make up the median region. For example, the mean regions N=48 shown by 402 are grouped into five median regions 404a, 404b, 404c, 404d, and 404e. According to an embodiment, using the five median regions improves performance by 9% compared to only using the 48 mean regions.

Pre-Processing by Discarding Noisy Facial Regions

Some of the facial regions may be severely corrupted by noise for a long time (e.g., due to occlusions or shadows), or they may not contain a physiologically strong iPPG signal (e.g., due to hair on the face). In such a case, the iPPG signals cannot be recovered from such corrupt regions, and including the corrupt regions in the vital sign estimation may corrupt the vital sign estimates. Therefore, it is beneficial to identify the corrupt regions and remove them before any processing, so that they don't affect the vital sign estimates.

To mitigate such a problem, some embodiments assume that the iPPG signals are relatively weak and slowly varying intensity variations. Therefore, any region that has large energy within a time window can be removed as likely containing noise. In some embodiments, the corrupt regions are removed with $\ell_2$ norms exceeding a threshold of $$\text{median}(\|P_t\|_2) + \frac{1}{2}\sigma(\|P_t\|_2)$$

where σ is a standard deviation, computed across the regions for each considered time window. The $\ell_2$ norm is computed over time, and the standard deviation is computed across the regions. In such a manner, the iPPG signals of a region from the set of iPPG signals are removed when the energy of the measured iPPG signals for the region within a time window is above a threshold.

Additionally, some facial regions are physiologically known to contain better iPPG signals. However, the "goodness" of these facial regions also depends on the particular video conditions, facial hair, or facial occlusions. Therefore, it is beneficial to identify which regions are likely to contain the most noise and remove them before any processing, so that they don't affect the vital sign estimates.

Figure 5:
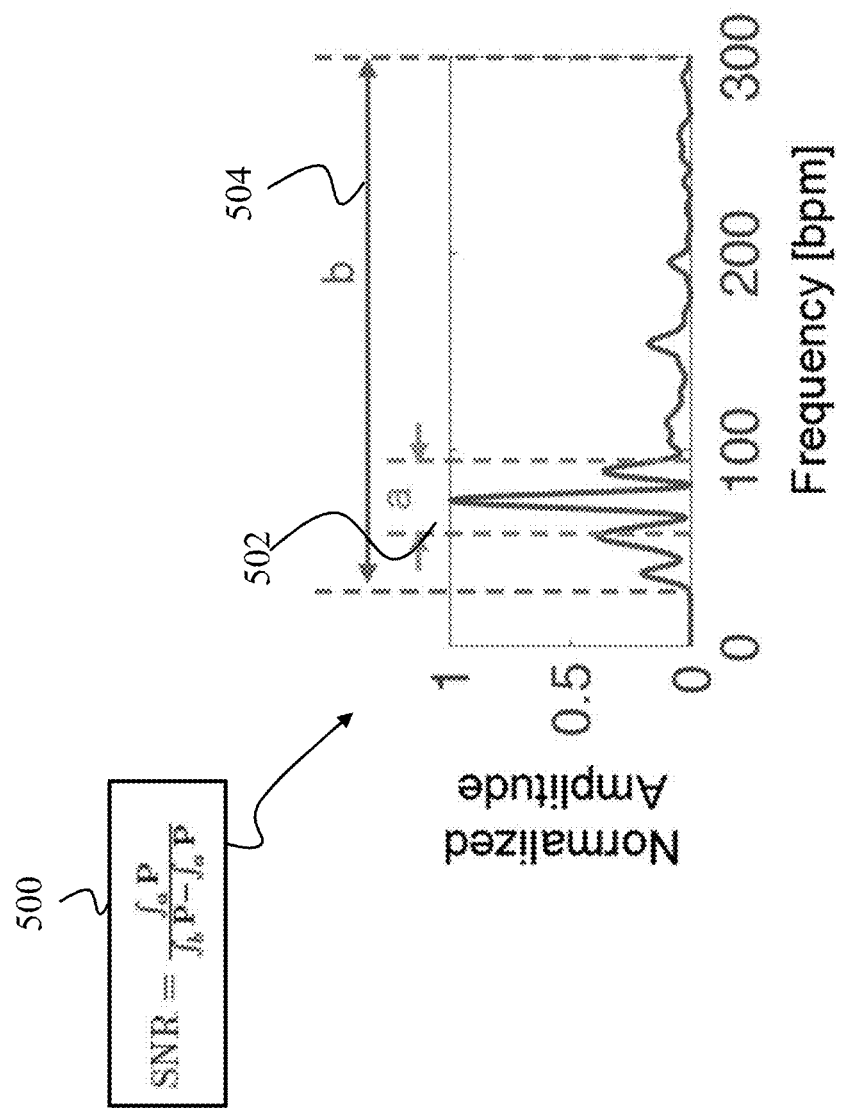
FIG. 5 shows a schematic of a power spectrum used for determining signal-to-noise ratio (SNR) of the iPPG signal used by some embodiments to evaluate usefulness of different regions.

FIG. 5 shows a schematic of a power spectrum curve used for determining signal-to-noise ratio (SNR) of the iPPG signal used by some embodiments to evaluate usefulness of different regions. For example, some embodiments do so by rejecting a region if its SNR is below a threshold $\theta_{SNR}$ (e.g., $\theta_{SNR}$=0.2) or if its maximum amplitude is above a threshold $\theta_{amp}$. For example, one embodiment sets $\theta_{amp}$ to be four times the average iPPG signal amplitude. Some embodiments determine the SNR 500 as the ratio of the area under the power spectrum curve in a region a 502 surrounding the maximum peak in a frequency spectrum, divided by the area under the curve in the rest of the frequency spectrum in a frequency range b 504 that contains the physiological range of the heartbeat signals (e.g., from 30 to 300 beats per minute (bpm)).

Fusion of Time Windows

Since the heartbeat signals vary slowly over time, the iPPG signals from multiple facial regions can be approximated to be a stationary process within a short time window. By using the information from previous time windows, iPPG signal denoising can be improved and a lot of abrupt changes caused by noise can be removed. The iPPG signals are processed using a sliding time window. For each time window, the iPPG signal to be processed is a weighted average of two sources: the previous time window's already processed and denoised data, and the current time window's noisy data that has not yet been processed. Such weighted average is defined as follows:

$$\overline{P} = \alpha \begin{bmatrix} P_o \\ P_n \end{bmatrix} + (1-\alpha) \begin{bmatrix} \tilde{Y}_o \\ P_o \end{bmatrix}.$$

Here, $$\begin{bmatrix} P_o \\ P_n \end{bmatrix}$$

represents the unprocessed, noisy data from current time window. $P_o$ denotes data from a portion of the current time window that overlaps with the previous (old) time window, while $P_n$ denotes data from a new portion of the current time window (the portion that does not overlap with the previous time window). The old data, $P_o$, were already processed (denoised) in the previous time step; the processed, denoised version of $P_o$ (which was output at the previous time step) is denoted by "$\tilde{Y}_o$". The parameter a controls how much the previous window's results are weighed. The smaller the value of a, the more is the consideration of the previous time window's results.

As part of the pre-processing within each time window, a different number of facial regions may be rejected, resulting in different dimensions of the iPPG signals in consecutive time windows. Therefore, after processing each time window, the signal in the missing regions is recomposed by linearly interpolating from neighboring regions in order to use the described weighted time window fusion.

Reducing Noise Using Orthogonal Projections

Figure 6A:
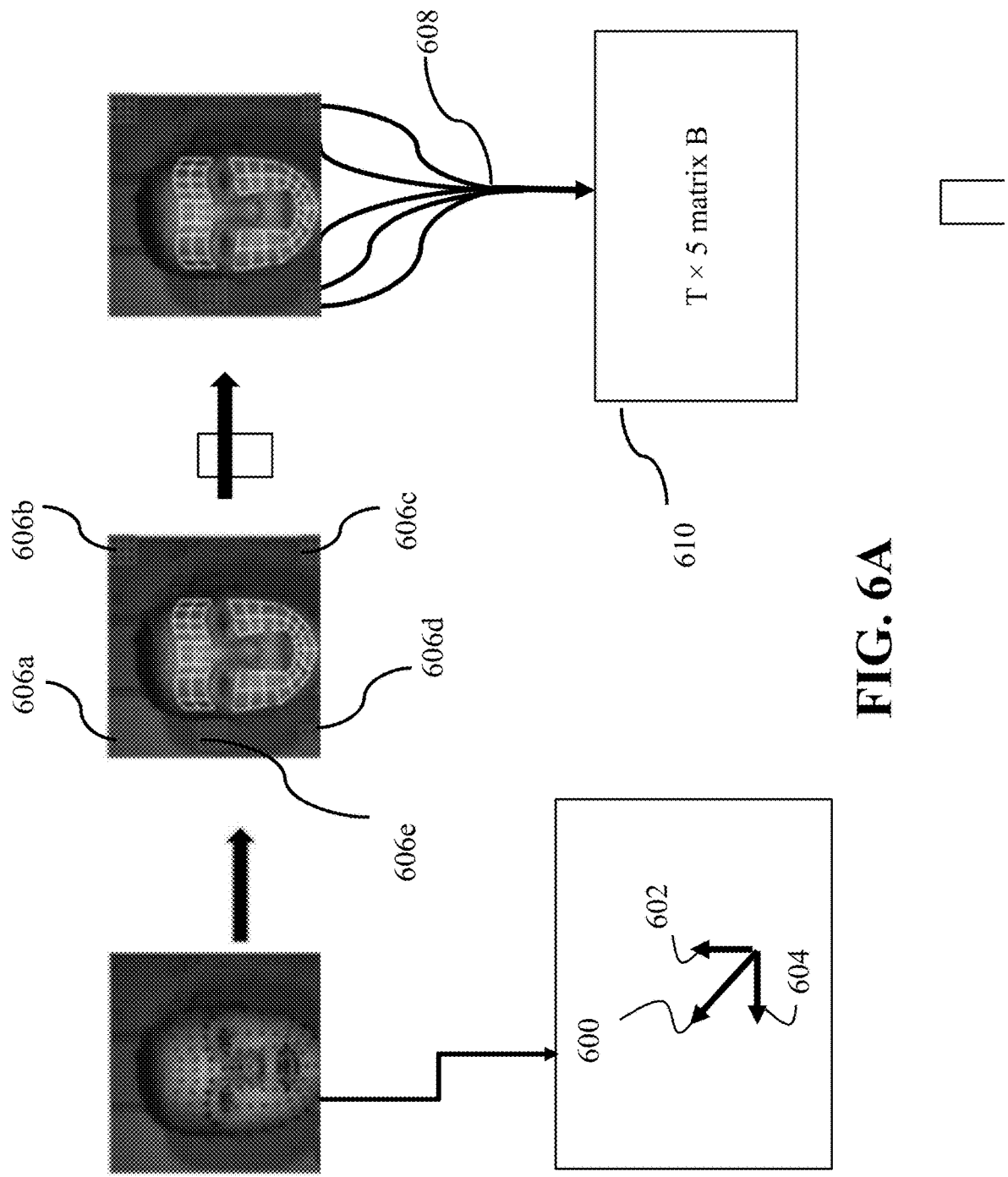
FIG. 6A shows a schematic of extraction of motion noise and a time-varying background illumination signal, according to some embodiments.

FIG. 6A shows a schematic of extraction of motion noise and a time-varying background illumination signal, according to some embodiments. Different facial regions may be noisy due various sources of measurement noise. For example, different facial regions may be contaminated differently by noise caused by changes in ambient illumination, motion alignment errors, and facial expressions, and as a result the noise may be high-dimensional. To that end, the iPPG signals from such noisy regions are also noisy. However, blood flows through facial regions with approximately a same temporal profile during a cardiac cycle. As a result, the underlying iPPG signal present in the measured intensity variations from all the median regions when grouped into a matrix corresponds to a low-rank matrix.

Some embodiments are based on realization that orthogonal projection (OP) of noisy iPPG signals P can be used to suppress the noise that is contaminating the iPPG signal. In other words, the noisy iPPG signals P can be denoised by using orthogonal projection (OP) of the noisy iPPG signals P. To that end, some embodiments orthogonally project the noisy iPPG signals P onto a noise subspace Q and subtract that projection from the noisy iPPG signals P. This is equivalent to projecting the noisy iPPG signals onto the orthogonal complement of the noise subspace. In some embodiments, the noise subspace Q includes one or more of a vertical motion signal V capturing a vertical motion of the regions producing the iPPG signals, a horizontal motion signal H capturing a horizontal motion of the regions producing the iPPG signals, and a background illumination signal B capturing light variation in background regions outside of the regions producing the iPPG signals.

To obtain the vertical motion signal V and the horizontal motion signal H, some embodiments extract a motion vector 600 for each facial landmark. The motion vector 600 can be resolved into two components, namely, a horizontal motion component 604 and a vertical motion component 602. The motion noise due to the motion of the face can be summarized with two time-varying 5-dimensional (5D) signals: a 5D horizontal motion signal H (corresponds to the horizontal motion signal H), and a 5D vertical motion signal V (corresponds to the vertical motion signal V).

To extract the 5D horizontal motion signal H, some embodiments measure horizontal motion of each of the (N=48) facial regions 402 by spatially averaging positions of four corners of the region in each frame. Further, the 48 dimensions are reduced to a lesser number of dimensions, for example, five dimensions, where each dimension is associated with the respective median region. The 48 dimensions are reduced to five dimensions by computing the median of the motion signals across the mean regions that belong to that median region. A sequence of the 5D signals across all time steps in the 10 second time window is a T×5 matrix H. In a similar manner, the 5D vertical motion signal V is computed.

Further, to approximate the noise caused by time-varying illumination at various locations, a 5D time-varying background illumination signal B (which corresponds to the background illumination signal B) is computed. To obtain the 5D time-varying background illumination signal B that represents the background ambient light intensity variation, a number of background regions are selected in the background not containing the face. For example, five background regions 606a, 606b, 606c, 606d, and 606e are selected. Each of the background regions is split into small (e.g., 30×30 pixel) regions. The spatial average of the intensity values of each small region is computed. Further, the median of the spatial averages of the intensity values of the small regions is computed to obtain a single value for the background region. Likewise, the median is obtained for each background region 608 in each frame, resulting in a T×5 matrix B 610.

Figure 6B:
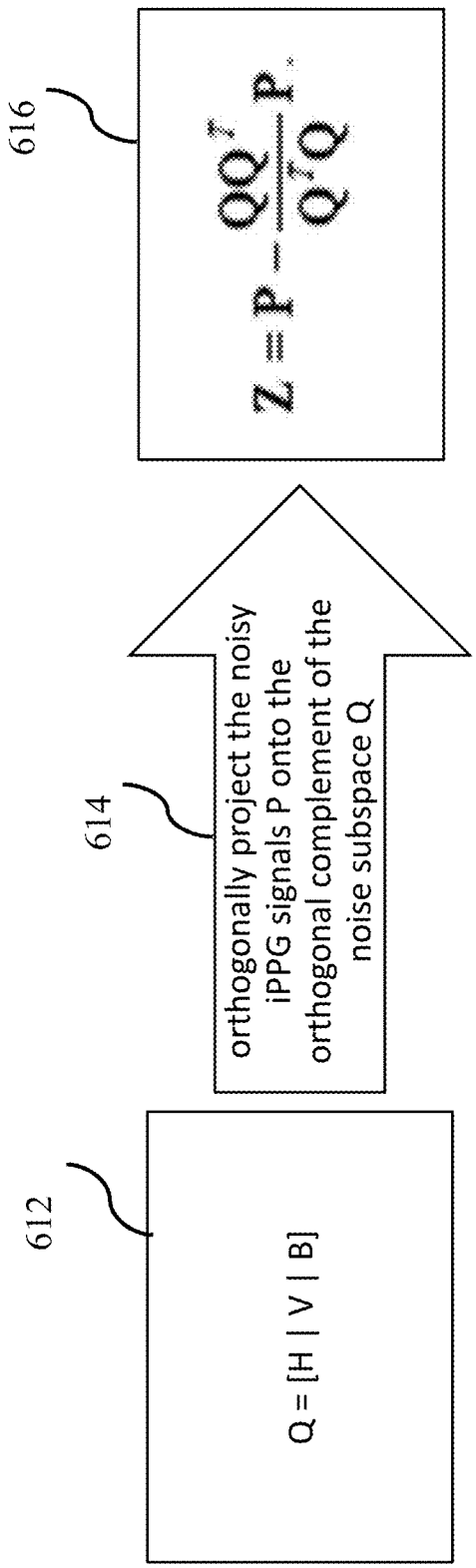
FIG. 6B shows a schematic an orthogonal projection of noisy iPPG signals to denoise the noisy iPPG signals, according to some embodiments.

FIG. 6B shows a schematic of the orthogonal projection of the noisy iPPG signals P to denoise the noisy iPPG signals, according to some embodiments. The three noise components (the 5D horizontal motion signal H, the 5D vertical motion signal V, and the 5D time-varying background illumination signal B) are concatenated to produce a noise signal matrix Q=[H|V|B] 612 of dimensions T×15. Some embodiments orthogonally project 614 the noisy iPPG signals P onto the noise subspace Q to produce an orthogonal projection of the noisy iPPG signals, and then subtract the orthogonal projection of the noisy iPPG signals from the noisy iPPG signals P to produce denoised iPPG signals Z 616:

$$Z = P - \frac{QQ^T}{Q^TQ}P.$$

wherein T is a matrix transpose operator. Note that this is equivalent to projecting the noisy iPPG signals P onto the orthogonal complement of the noise subspace Q.

Some embodiments are based on realization that the denoised iPPG signals Z can be used in two-one norm regularization for recovering the iPPG signal's sparse frequency spectrum (X).

Figure 7:
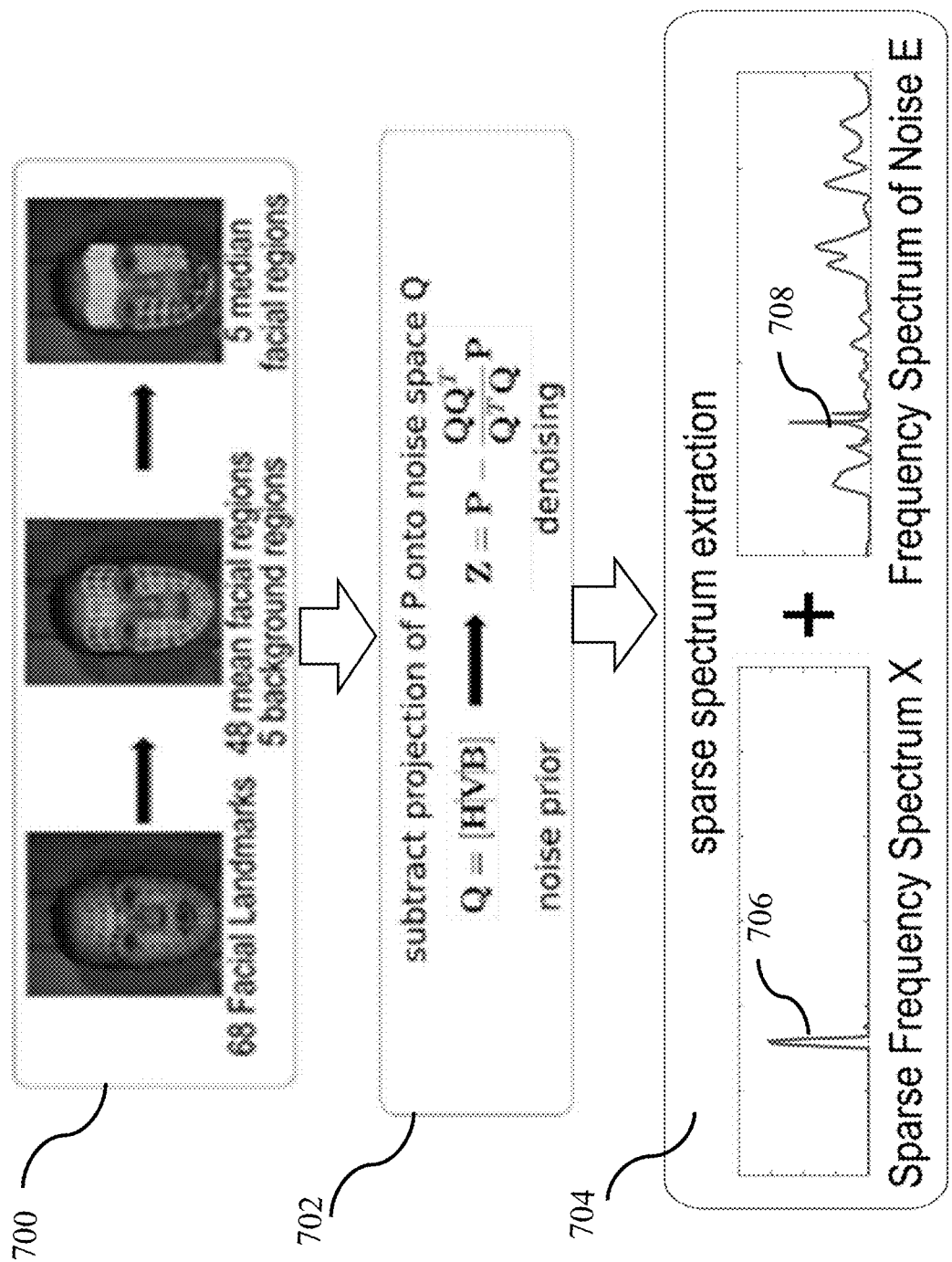
FIG. 7 shows a schematic of an AutoSparsePPG framework using denoised iPPG signals, according to some embodiments.

FIG. 7 shows a schematic of the AutoSparsePPG framework using the denoised iPPG signals Z, according to some embodiments. At block 700, the iPPG signals are computed from each facial region as described above with reference to FIG. 4. The iPPG signals are noisy due to the measurement noise. To denoise the noisy iPPG signals, at block 702, the motion noise (H, V) and the noise B from the light variations in the background regions are suppressed by orthogonally projecting the noisy iPPG signals P onto the noise subspace Q, and then subtracting the orthogonal projection of the noisy iPPG signals from the noisy iPPG signals P (explained in detail above with reference to FIGS. 6A and 6B). Consequently, the denoised iPPG signals Z are produced. At block 704, the denoised iPPG signals Z can be used for the sparse spectrum extraction. Specifically, the denoised iPPG signals Z are modeled as a sum of two components: the desired iPPG signal Y, whose frequency spectrum, X, has only a few non-zero frequency coefficients; and an inlier noise, E, that was not removed by the denoising 702. In an embodiment, the denoised iPPG signal Z is used as one of the inputs to the AutoSparsePPG algorithm (shown in FIG. 2A) to recover the iPPG signal's sparse frequency spectrum 706 and a frequency spectrum of noise 708.

Some embodiments aim to provide accurate estimation of the vital signs even in volatile environments where there is dramatic illumination variation. For example, in a volatile environment such as an in-vehicle environment, some embodiments provide an RPPG system suitable for estimating vital signs of a driver or passenger of a vehicle. However, during driving, illumination on a person's face can change dramatically. For example, during the day, sunlight is filtered by trees, clouds, and buildings before reaching the driver's face. As the vehicle moves, the direct illumination can change frequently and dramatically in both magnitude and spatial extent. At night, overhead streetlamps and headlights of approaching cars cause large-intensity, spatially non-uniform changes in illumination. Such illumination changes can be so dramatic and omnipresent that a number of approaches to mitigate these illumination variations are not practical.

To address these challenges, additionally or alternatively to sparse reconstruction with joint sparsity disclosed above, one embodiment uses active in-car illumination, in a narrow spectral band in which the sunlight, streetlamp, and headlight and taillight spectral energy are all minimal.

Figure 8:
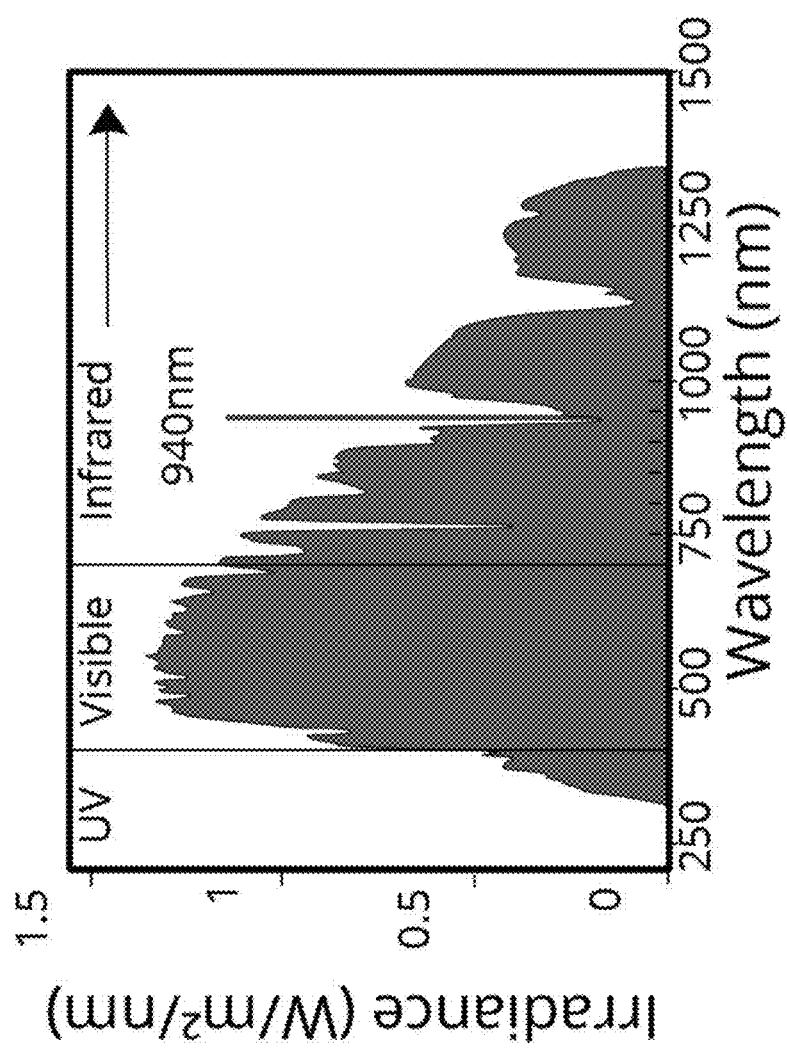
FIG. 8 shows a plot of a spectrum of sunlight at Earth's surface used by some embodiments.

FIG. 8 shows a plot of a spectrum of sunlight at Earth's surface used by some embodiments. For example, due to water in atmosphere, the sunlight that reaches the earth's surface has much less energy around the near-infrared (NIR) wavelength of 940 nm than it does at other wavelenghts. The light output by the streetlamps and vehicle lights (such as headlights) is typically in the visible spectrum, with very little power at infrared frequencies. To that end, one embodiment uses an active narrow-band illumination source at or near 940 nm and a narrow-band camera filter overlapping the wavelengths of the narrow-band illumination source, which ensures that much of the illumination changes due to environmental ambient illumination are filtered away. Further, since this narrow frequency band at or near 940 nm is beyond the visible range, humans do not perceive this light source and thus are not distracted by its presence. Moreover, the narrower the bandwidth of the light source used in the active illumination, the narrower the bandpass filter on the camera can be, which further rejects changes due to ambient illumination. For example, some implementations use an LED source and camera bandpass filters with 10 nm bandwidth.

Accordingly, one embodiment uses a narrow-bandwidth near-infrared (NIR) light source to illuminate the skin of the person at a narrow frequency band including a near-infrared frequency of 940 nm and an NIR camera to measure the intensities of different regions of the skin in the narrow frequency band.

Some embodiments are based on recognition that in the narrow frequency band including the near-infrared frequency of 940 nm, the signal observed by the NIR camera is significantly weaker than a signal observed by a color intensity camera, such as an RGB camera. However, experiments demonstrated the effectiveness of the sparse reconstruction RPPG used by some embodiments in handling these weak intensity signals.

Figure 9:
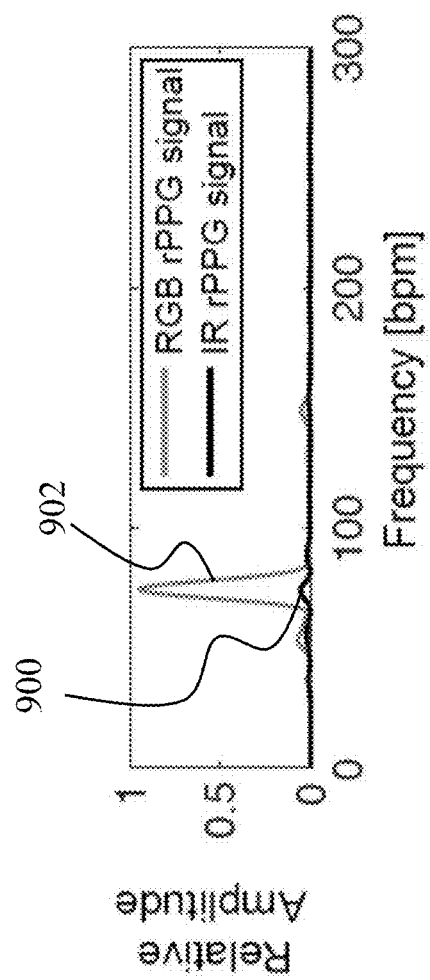
FIG. 9 shows a plot for comparison of iPPG signal frequency spectrum in near-infrared (IR) and RGB.

FIG. 9 shows a plot for comparison of iPPG signal frequency spectrums obtained experimentally in NIR) and in the visible portion of the spectrum (RGB). The iPPG signal in NIR 900 (labeld "IR rPPG signal" in the legend) is about 10 times weaker than in RGB 902 (labeled "RGB iPPG signal"). Therefore, the RPPG system of one embodiment includes a near-infrared (NIR) light source to illuminate the skin of the person, wherein the NIR light source provides illumination in a first frequency band, and a camera to measure the intensities of each of the different regions in a second frequency band overlapping the first frequency band, such that the measured intensities of a region of the skin are computed from intensities of pixels of an image of the region of the skin.

The first frequency band and the second frequency band include a near-infrared frequency of 940 nm. The system includes a filter to denoise the measurements of the intensities of each of the different regions using robust principal components analysis (RPCA). In an embodiment, the second frequency band, which in one embodiment is determined by a bandpass filter on the camera, has a passband of width less than 20 nm, e.g., the bandpass filter has a narrow passband whose full width at half maximum (FWHM) is less than 20 nm. In other words, the overlap between the first frequency band and the second frequency band is less than 20 nm wide. Such a system in combination with sparse reconstruction is able to perform RPPG for the volatile environment. In other embodiments, the bandpass filter has a wider passband, e.g., a passband whose FWHM is approximately 50 nm.

Some embodiments incorporate the realization that optical filters such as bandpass filters and long-pass filters (i.e., filters that block transmission of light whose wavelength is less than a cutoff frequency but allow transmission of light whose wavelength is greater than a second, often equal, cutoff frequency) may be highly sensitive to an angle of incidence of the light passing through the filter. For example, an optical filter may be designed to transmit and block specified frequency ranges when the light enters the optical filter parallel to the axis of symmetry of the optical filter (roughly perpendicular to the optical filter's surface), which we will call an angle of incidence of 0°. When an angle of incidence varies from 0°, many optical filters exhibit "blue shift," in which the passband and/or cutoff frequencies of the filter effectively shift to shorter wavelengths. To account for the blue shift phenomenon, some embodiments use a center frequency of the overlap between the first and second frequency bands to have a wavelength greater than 940 nm (e.g., they shift the center frequency of a bandpass optical filter or the cutoff frequencies of a long-pass optical filter to have a longer wavelength than 940 nm).

Furthermore, because light from different parts of the skin will be incident upon the optical filter at different angles of incidence, the optical filter allows different transmission of the light from different parts of the skin. To compensate this, some embodiments use a bandpass filter with a wider passband, e.g., the bandpass optical filter has a passband that is wider than 20 nm, and hence the overlap between the first and second frequency bands is greater than 20 nm wide.

Illumination intensity across the face can be non-uniform due to variation in 3D directions of normals across the face surface, due to shadows cast on the face, and due to different parts of the face being at different distances from the NIR light source. To make the illumination more uniform across the face, some embodiments use a number of NIR light sources, for example, two NIR light sources, placed on each side of the face and at approximately equal distances from the head. In addition, horizontal and vertical diffusers are placed on the NIR light sources to widen the light beams reaching the face, to minimize the illumination intensity difference between the center of the face and the periphery of the face.

Some embodiments aim to capture well-exposed images of the skin regions in order to measure strong iPPG signals. However, the intensity of the illumination is inversely proportional to square of a distance from the light source to the face. If the person is too close to the light source, the images become saturated and may not contain the iPPG signals. If the person is at a farther distance from the light source, the images will become dimmer and have weaker iPPG signals. Some embodiments experimentally select the most favorable position of the light sources and their brightness setting to avoid capturing saturated images, while recording well-exposed images at a range of possible distances between the skin regions of the person and the camera.

Therefore, an RPPG system uses the narrow frequency band including the near-infrared frequency of 940 nm to reduce the noise due to illumination variations, and the AutoSparsePPG framework (described above with reference to FIG. 7) robust to the motion noise. As a result, the RPPG system provides accurate estimation of the vital signs of the person.

Figure 10:
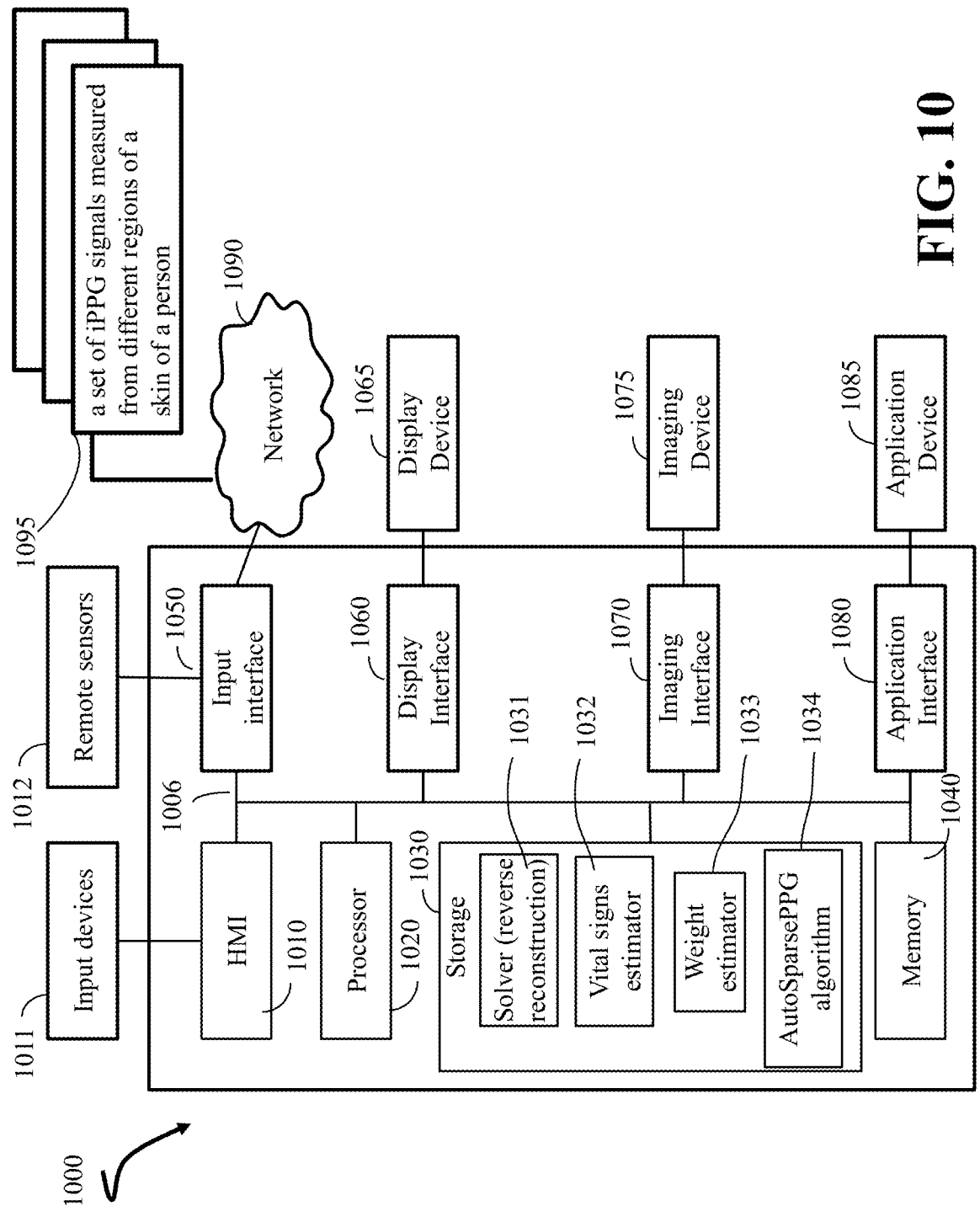
FIG. 10 shows a block diagram of a remote photoplethysmography (RPPG) system, according to some embodiments.

FIG. 10 shows a block diagram of a remote photoplethysmography (RPPG) system 1000 in accordance with some embodiments. The system 1000 includes a processor 1020 configured to execute stored instructions, as well as a memory 1040 that stores instructions that are executable by the processor. The processor 1020 can be a single core processor, a multi-core processor, a computing cluster, or any number of other configurations. The memory 1040 can include random access memory (RAM), read only memory (ROM), flash memory, or any other suitable memory systems. The processor 1020 is connected through a bus 1006 to one or more input and output devices.

The instructions stored in the memory 1040 implement an RPPG method for estimating the vital signs of the person from a set of imaging photoplethysmography (iPPG) signals measured from different regions of a skin of a person. The RPPG system 1000 can also include a storage device 1030 configured to store various modules such as solver 1031, vital sign estimator 1032, weight estimator 1033, and AutoSparsePPG algorithm 1034. The aforesaid modules stored in the storage device 1030 are the executed by the processor 1020 to perform the vital signs estimations. The vital sign corresponds to a pulse rate of the person or heart rate variability of the person. The storage device 1030 can be implemented using a hard drive, an optical drive, a thumb drive, an array of drives, or any combinations thereof.

According to some principles employed by different embodiments, the solver 1031 solves an optimization problem to determine frequency coefficients at the frequency bins of the quantized frequency spectrum of the measured iPPG signals by minimizing a distance between the measured iPPG signals and corresponding iPPG signals reconstructed from the determined frequency coefficients while enforcing joint sparsity of the determined frequency coefficients. Such a reverse reconstruction of the frequency coefficients allows enforcing a common metric, i.e., the joint sparsity, in the frequency domain. According to some other principles employed by different embodiments, the solver 1030 determines frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have the non-zero values at the same frequency bins.

The vital sign estimator 1032 is configured to estimate the vital signs of the person from the determined frequency coefficients of the measured iPPG signals. Additionally, the RPPG system 1000 includes a weight estimator 1033 configured determine weights of the frequency bins indicative of locations of the frequency bins having the frequency coefficients with the non-zero values based on a function of the phase differences across the measured iPPG signals. The AutoSparsePPG algorithm 1034 is used for sparse spectrum estimation.

The system 1000 includes an input interface 1050 to receive a set of imaging photoplethysmography (iPPG) signals measured from different regions of a skin of a person. For example, the input interface can be a network interface controller adapted to connect the RPPG system 1000 through the bus 1006 to a network 1090. Through the network 1090, the values of intensity measurements 1095 can be downloaded and stored as intensity values 1034 within the computer's storage system 1030 for storage and/or further processing.

Additionally or alternatively, in some implementations, the RPPG system 1000 is connected to a remote sensor 1012, such as a camera, to collect the iPPG signals 1034. In some implementations, a human machine interface (HMI) 1010 within the system 1000 connects the system to input devices 1011, such as a keyboard, a mouse, trackball, touchpad, joy stick, pointing stick, stylus, touchscreen, and among others.

The RPPG system 1000 can be linked through the bus 1006 to an output interface to render the vital signs of the person. For example, the RPPG system 1000 can include a display interface 1060 adapted to connect the system 1000 to a display device 1065, wherein the display device 1065 can include a computer monitor, camera, television, projector, or mobile device, among others.

The RPPG system 1000 can also include and/or be connected to an imaging interface 1070 adapted to connect the RPPG system 1000 to an imaging device 1075. The imaging device 1075 can include a video camera, computer, mobile device, webcam, or any combination thereof.

In some embodiments, the RPPG system 1000 is connected to an application interface 1080 through the bus 1006 adapted to connect the RPPG system 1000 to an application device 1085 that can operate based on results of remote photoplethysmography. For example, in one embodiment, the device 185 is a car navigation system that uses the vital signs of a person to decide how to control, e.g., steer, the car. In other embodiments, the device 185 is a driver monitoring system, which uses the vital signs of the driver to determine when the driver is able to drive safely, e.g., whether the driver is drowsy or not.

Figure 11:
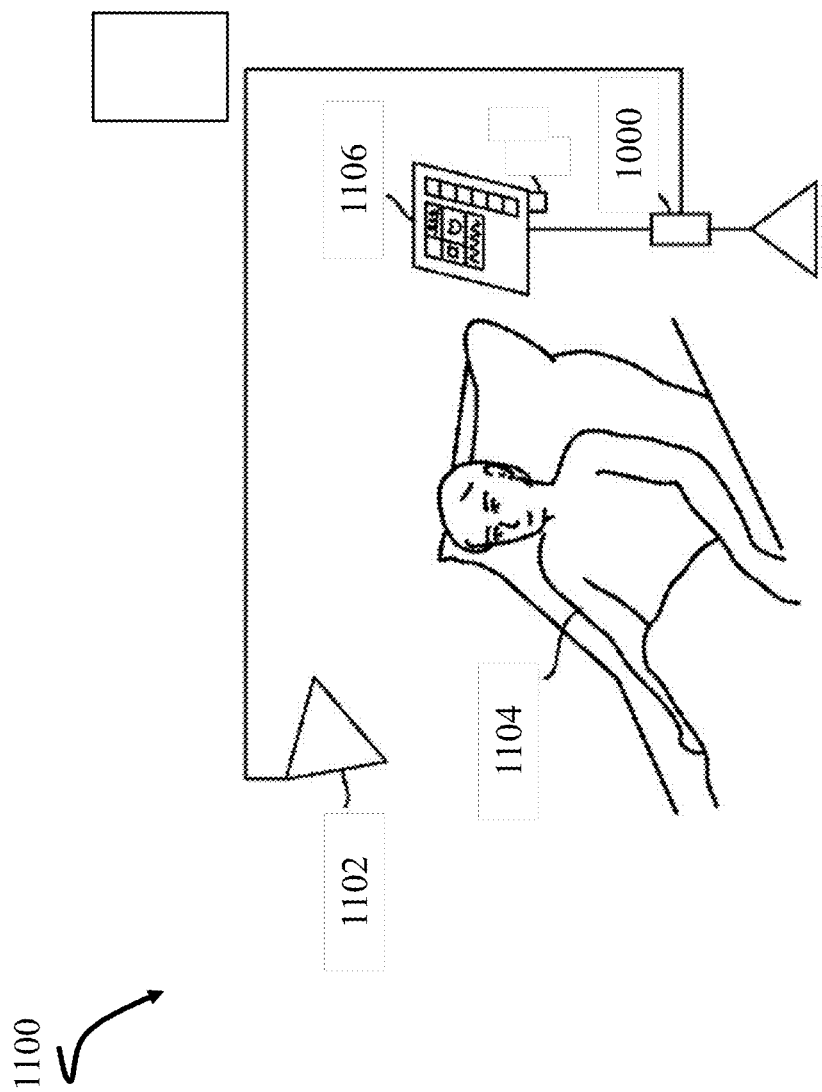
FIG. 11 shows a schematic of a patient monitoring system using the RPPG system, in a hospital scenario, according to some embodiments.

FIG. 11 shows of a schematic a patient monitoring system 1100 using the RPPG system 1000, in a hospital scenario, according to some embodiments. A patient 1104 is lying on a hospital bed. In such a hospital scenario, the vital signs of the patient 1104 need to be remotely monitored. The patient monitoring system 1100 use the remote photoplethysmographic measurement principle. The measurements of the vital signs with a camera are known as imaging photoplethysmography (iPPG). Thereby, a camera 1102 is used to capture an image, i.e., a video sequence of the patient 1104.

The camera 1102 can include a CCD or CMOS sensor for converting incident light and the intensity variations thereof into an electronic signal. The camera 1102 particularly non-invasively captures light reflected from a skin portion of the patient 10. A skin portion may thereby particularly refer to the forehead, neck, wrist, part of the arm, or some other portion of the patient's skin. A light source, e.g. a near-infrared light source, may be used to illuminate the patient or a region of interest including a skin portion of the patient.

Based on the captured images, the RPPG system 1000 determines the vital signs of the patient 1104. In particular, the RPPG system 1000 determines the vital signs such as the heart rate, the breathing rate or the blood oxygenation of the patient 1104. Further, the determined vital signs are usually displayed on an operator interface 1106 for presenting the determined vital signs. Such an operator interface 1106 may be a patient bedside monitor or may also be a remote monitoring station in a dedicated room in a hospital or even in a remote location in telemedicine applications.

Figure 12:
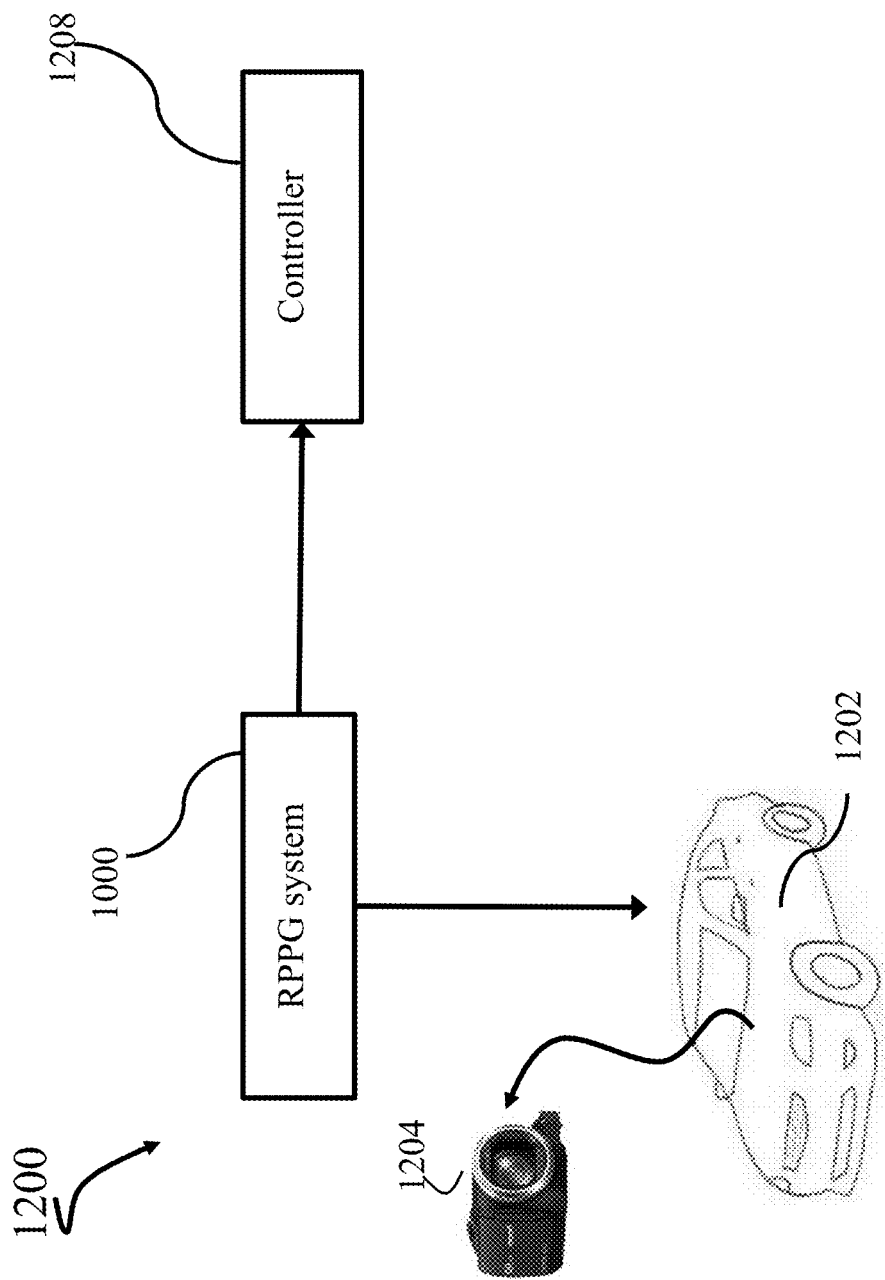
FIG. 12 shows a schematic of a driver assistance system using the RPPG system, according to some embodiments.

FIG. 12 shows a schematic of a driver assistance system 1200 using the RPPG system 1000, according to some embodiments. The NIR light source and/or a NIR camera 1204 are arranged in a vehicle 1202. The NIR light source is arranged in the vehicle 1202 to illuminate skin of a person driving the vehicle (driver), and the NIR camera 1204 is arranged in the vehicle to measure the iPPG signals from different regions of the skin of the driver. The RPPG system 1000 is integrated into the vehicle 1202. The RPPG system 1000 receives the measured iPPG signals and determines the vital sign, such as pulse rate, of the driver.

Further, the processor of RPPG system 1000 may produce one or more control action commands, based on the estimated vital signs of the person driving the vehicle. The one or more control action commands includes vehicle braking, steering control, generation of an alert notification, initiation of an emergency service request, or switching of a driving mode. The one or more control action commands are transmitted to a controller 1208 of the vehicle 1202. The controller 1208 may control the vehicle 1202 according to one or more control action commands. For example, if the determined pulse rate of the driver is very low, then the driver may be experiencing a heart attack. Consequently, the RPPG system 1000 may produce control commands for reducing a speed of the vehicle and/or steering control (e.g., to steer the vehicle to a shoulder of a highway and make it come to a halt) and/or initiate an emergency service request. Accordingly, the controller 1208 may control the vehicle.

The above description provides exemplary embodiments only, and is not intended to limit the scope, applicability, or configuration of the disclosure. Rather, the above description of the exemplary embodiments will provide those skilled in the art with an enabling description for implementing one or more exemplary embodiments. Contemplated are various changes that may be made in the function and arrangement of elements without departing from the spirit and scope of the subject matter disclosed as set forth in the appended claims.

Specific details are given in the above description to provide a thorough understanding of the embodiments. However, understood by one of ordinary skill in the art can be that the embodiments may be practiced without these specific details. For example, systems, processes, and other elements in the subject matter disclosed may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but may have additional steps not discussed or included in a figure. Furthermore, not all operations in any particularly described process may occur in all embodiments. A process may correspond to a method, a function, a procedure, a subroutine, a subprogram, etc. When a process corresponds to a function, the function's termination can correspond to a return of the function to the calling function or the main function.

Furthermore, embodiments of the subject matter disclosed may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. Typically, the functionality of the program modules may be combined or distributed as desired in various embodiments.

Embodiments of the present disclosure may be embodied as a method, of which an example has been provided. The acts performed as part of the method may be ordered in any suitable way. Accordingly, embodiments may be constructed in which acts are performed in an order different than illustrated, which may include performing some acts concurrently, even though shown as sequential acts in illustrative embodiments. Although the present disclosure has been described with reference to certain preferred embodiments, it is to be understood that various other adaptations and modifications can be made within the spirit and scope of the present disclosure. Therefore, it is the aspect of the append claims to cover all such variations and modifications as come within the true spirit and scope of the present disclosure.

The invention claimed is:

1. A remote photoplethysmography (RPPG) system for estimating vital signs of a person, comprising: at least one processor; and memory having instructions stored thereon that, when executed by the at least one processor, cause the RPPG system to:
   receive a set of imaging photoplethysmography (iPPG) signals measured from different regions of a skin of a person;
   determine a sparsity level constraint indicative of a number of frequency bins of a quantized frequency spectrum of the measured iPPG signals having non-zero values of frequency coefficients;
   determine frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have the non-zero values at the same frequency bins; and
   output one or a combination of the determined frequency coefficients, the iPPG signals reconstructed from the determined frequency coefficients, and a vital sign signal corresponding to the reconstructed iPPG signals.

2. The RPPG system of claim 1, wherein the sparsity level constraint is determined adaptively based on a function of intensities in the measured iPPG signals as a bound on the minimum energy that a jointly sparse signal embedded in the measured iPPG signals can hold, and wherein the sparsity level constraint enforces an upper bound on energy levels of the determined frequency coefficients of the reconstructed iPPG signals.

3. The RPPG system of claim 2, wherein the measured iPPG signals are subject to measurement noise, and wherein the bound on the minimum energy of the jointly sparse signal embedded in the measured iPPG signals is determined iteratively by minimizing energy deviation based on a gradient of the distance of the reconstructed iPPG signals to the measured iPPG signals, wherein the gradient is computed with respect to the frequency coefficients and the measurement noise.

4. The RPPG system of claim 1, wherein the processor is further configured to execute a two-one norm regularization of a frequency matrix of the frequency coefficients determined for reconstructing the iPPG signals modified with a noise matrix of measurement noise, and wherein the two-one norm regularization is applied to opposite dimensions of the frequency matrix and the noise matrix.

5. The RPPG system of claim 4, wherein a first dimension of the frequency matrix corresponds to the different regions of the skin of the person, wherein a second dimension of the frequency matrix corresponds to frequency bins of the frequency coefficients, wherein a first dimension of the noise matrix corresponds to the different regions of the skin of the person, wherein a second dimension of the noise matrix corresponds to a time of the measurements, and wherein the two-one norm regularization is applied to opposite dimensions such that two-norm along the first dimension of the frequency matrix is followed by a one-norm along the second dimension of the frequency matrix, while a two-norm along the second dimension of the noise matrix is followed by a one-norm along the first dimension of the noise matrix.

6. The RPPG system of claim 1, wherein the sparsity level constraint is enforced by a regularization parameter that is determined iteratively in response to updated estimates of the reconstructed iPPG signals to ensure that energy of the frequency coefficients of the reconstructed iPPG signals equals the sparsity level constraint.

7. The RPPG system of claim 1, wherein the processor is further configured to:
  determine weights of the frequency bins indicative of which of the frequency bins have the frequency coefficients with the non-zero values based on a function of the phase differences across the measured iPPG signals; and
  enforce the joint sparsity by encouraging the number of non-zero frequency coefficients indicated by the sparsity level constraint to be at the locations indicated by the weights of the frequency bins.

8. The RPPG system of claim 7, wherein the processor is further configured to execute a weighted two-one norm regularization of a frequency matrix of the frequency coefficients determined for reconstructing the iPPG signals modified with a noise matrix of measurement noise, and wherein the weighted two-one norm regularization is applied to opposite dimensions of the frequency matrix and the noise matrix.

9. The RPPG system of claim 8, wherein a first dimension of the frequency matrix corresponds to the different regions of the skin of the person, wherein a second dimension of the frequency matrix corresponds to frequency bins of the frequency coefficients, wherein a first dimension of the noise matrix corresponds to the different regions of the skin of the person, wherein a second dimension of the noise matrix corresponds to a time of the measurements, and wherein the weighted two-one norm regularization is applied to opposite dimensions such that two-norm along the first dimension of the frequency matrix is followed by a weighted one-norm along the second dimension of the frequency matrix, while a two-norm along the second dimension of the noise matrix is followed by a weighted one-norm along the first dimension of the noise matrix.

10. The RPPG system of claim 9, wherein weights in the weighted one-norm along the first dimension of the noise matrix are identical.

11. The RPPG system of claim 9, wherein weights in the weighted one-norm along the second dimension of the frequency matrix are identical, and wherein weights in the weighted one-norm along the first dimension of the noise matrix are identical.

12. The RPPG system of claim 9, wherein the weights in the weighted one-norm along the second dimension of the frequency matrix are a function of the phase differences across the measured iPPG signals from different regions.

13. The RPPG system of claim 1, wherein to obtain the measured iPPG signals, the processor is further configured to:
  receive a set of iPPG signals measured from a set of skin regions of the person;
  group the set of iPPG signals into median regions to produce a clustering of iPPG signals; and
  compute a measured iPPG signal for each median region that is a median across the iPPG signals measured from the skin regions that form the median region.

14. The RPPG system of claim 13, wherein the processor is further configured to remove iPPG signals of a region from the set of iPPG signals when energy of the measured iPPG signals for the region within a time window is above a threshold.

15. The RPPG system of claim 13, wherein the iPPG signals in the set of iPPG signals are noisy due to measurement noise, and wherein the processor is further configured to denoise the noisy iPPG signals in the set of iPPG signals by projecting the noisy iPPG signals onto an orthogonal complement of a noise subspace.

16. The RPPG system of claim 15, wherein to project the noisy iPPG signals P onto the orthogonal complement of the noise subspace Q, the processor is further configured to orthogonally project the noisy iPPG signals P onto the noise subspace Q to produce an orthogonal projection of the noisy iPPG signals, and then subtract the orthogonal projection of the noisy iPPG signals from the noisy iPPG signals P to produce denoised iPPG signals Z.

17. The RPPG system of claim 15, wherein the noise subspace Q includes a vertical motion signal V capturing a vertical motion of the regions producing the iPPG signals, a horizontal motion signal H capturing a horizontal motion of the regions producing the iPPG signals, and a background illumination signal B capturing light variation in background regions outside of the regions producing the iPPG signals.

18. The RPPG system of claim 15, wherein the noise subspace Q=[H|V|B], and wherein the denoised iPPG signals Z are determined according to $$Z = P - \frac{QQ^T}{Q^T Q} P,$$

wherein T is a matrix transpose operator.

19. The RPPG SYSTEM of claim 1, wherein the intensities of different regions of the skin of the person are measured in a frequency band including a near-infrared frequency corresponding to a wavelength 940 nm.

20. The RPPG system of claim 1, wherein the vital sign is a pulse rate of the person.

21. The RPPG system of claim 1, wherein the vital sign is a heart rate variability of the person.

22. The RPPG system of claim 1, wherein the person corresponds to a driver of a vehicle, and wherein the processor is further configured to produce one or more control action commands for a controller of the vehicle, based on the vital sign of the driver.

23. The RPPG system of claim 22, wherein the one or more control action commands includes vehicle braking, steering control, generation of an alert notification, initiation of an emergency service request, or switching of a driving mode.

24. A remote photoplethysmography (RPPG) method for estimating vital signs of a person, comprising:
  receiving a set of imaging photoplethysmography (iPPG) signals measured from different regions of a skin of a person;
  determining a sparsity level constraint indicative of a number of frequency bins of a quantized frequency spectrum of the measured iPPG signals having non-zero values of frequency coefficients;

determining frequency coefficients at the frequency bins of the quantized frequency spectrum of the measured iPPG signals by minimizing a distance between the measured iPPG signals and corresponding iPPG signals reconstructed from the determined frequency coefficients, while enforcing joint sparsity of the determined frequency coefficients subject to the sparsity level constraint, such that the determined frequency coefficients of different iPPG signals have the non-zero values at the same frequency bins; and outputting one or a combination of the determined frequency coefficients, the iPPG signals reconstructed from the determined frequency coefficients, and a vital sign signal corresponding to the reconstructed iPPG signals.

* * * * *